(12) United States Patent
McCown et al.

(10) Patent No.: US 12,076,351 B2
(45) Date of Patent: Sep. 3, 2024

(54) AAV VECTORS TARGETED TO OLIGODENDROCYTES

(71) Applicant: The University of North Carolina at Chapel Hill, Chapel Hill, NC (US)

(72) Inventors: Thomas McCown, Carrboro, NC (US); Steven Gray, Southlake, TX (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/511,913

(22) Filed: Jul. 15, 2019

(65) Prior Publication Data

US 2019/0328804 A1    Oct. 31, 2019

Related U.S. Application Data

(62) Division of application No. 15/488,966, filed on Apr. 17, 2017, now abandoned, which is a division of application No. 14/431,900, filed as application No. PCT/US2013/062240 on Sep. 27, 2013, now Pat. No. 9,636,370.

(60) Provisional application No. 61/707,108, filed on Sep. 28, 2012.

(51) Int. Cl.
| | | |
|---|---|---|
| *C12N 15/86* | (2006.01) | |
| *A61K 9/00* | (2006.01) | |
| *A61K 35/76* | (2015.01) | |
| *C07K 14/005* | (2006.01) | |
| *C12N 7/00* | (2006.01) | |
| *A61K 39/23* | (2006.01) | |
| *C07K 14/015* | (2006.01) | |
| *C12N 15/864* | (2006.01) | |

(52) U.S. Cl.
CPC ............ *A61K 35/76* (2013.01); *A61K 9/0085* (2013.01); *C07K 14/005* (2013.01); *C12N 7/00* (2013.01); *C12N 15/86* (2013.01); *A61K 39/23* (2013.01); *C07K 14/015* (2013.01); *C12N 15/8645* (2013.01); *C12N 2750/14122* (2013.01); *C12N 2750/14142* (2013.01); *C12N 2750/14143* (2013.01); *C12N 2750/14145* (2013.01); *C12N 2810/6027* (2013.01)

(58) Field of Classification Search
CPC ................ C12N 15/86; C12N 15/8645; C12N 2750/14142; C12N 2750/14143; C12N 2750/14122; C12N 15/63; A61K 48/005; A61K 9/0085; C07H 21/04
See application file for complete search history.

(56) References Cited

U.S. PATENT DOCUMENTS

| | | |
|---|---|---|
| 5,478,745 A | 12/1995 | Samulski et al. |
| 6,503,888 B1 | 1/2003 | Kaplitt et al. |
| 8,445,267 B2 | 5/2013 | Zhong et al. |
| 2003/0228282 A1 | 12/2003 | Gao et al. |
| 2012/0009268 A1 | 1/2012 | Asokan et al. |
| 2012/0202745 A1 | 8/2012 | O'Shea et al. |

FOREIGN PATENT DOCUMENTS

| | | |
|---|---|---|
| CA | 2465868 A1 | 5/2003 |
| EP | 2345731 | 7/2011 |
| JP | 2005512533 | 5/2005 |
| WO | 03/052051 | 6/2003 |
| WO | 2004108922 A2 | 12/2004 |
| WO | 2006/110689 | 10/2006 |
| WO | WO 2009/013290 A1 * | 1/2009 |

OTHER PUBLICATIONS

Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Cruz et al., 2017, Methods in Molecular Biology, vol. 1654, Chapter 5, pp. 55-75.*
Gao et al., 2002 (PNAS, vol. 99, No. 18, p. 11854-11859).*
Gao et al., 2002 (GenEMBL Accession No. AF513852, computer printout, pp. 1-5) (Gao GenEMBL).*
Asari et al. "Efficient transduction of oligodendrocytes with AAV8 vectors", The 50th Annual meeting of the Japan Neuroscience Society Conference (Yokohama) (2007) vol. 46, Nos. 2-3, p. 424, O2P-K01.
Chen et al. "Oligodendrocyte-Specific Gene Expression In Mouse Brain: Use of a Myelin-Forming Cell Type-Specific Promoter in an Adeno-Associated Virus", J. Neuroscience Research 55:504-513 (1999).
Extended European Search Report corresponding to European Application No. 13841643.3 issued Apr. 11, 2016.
Gao et al. "Adeno-associated virus 8 nonstructural protein and capsid protein genes, complete cds", GenBank [online], Accession No. AF513852 (2002) 2 pages.
Gao et al. "Novel adeno-associated viruses from rhesus monkeys as vectors for human gene therapy", PNAS 99 (18):11854-11859 (2002).
Gao et al., 2003, A_Geneseq Accession No. ABR62759, computer printout pp. 11-13.

(Continued)

*Primary Examiner* — Shin Lin Chen
(74) *Attorney, Agent, or Firm* — Myers Bigel, P.A.

(57) ABSTRACT

The invention relates to chimeric AAV capsids targeted to oligodendrocytes and virus vectors comprising the same. The invention further relates to methods of delivering a nucleic acid of interest to an oligodendrocyte in vitro and in vivo, methods of delivering a nucleic acid of interest to an area of the CNS bordering a compromised blood-brain barrier, and methods of treating disorders associated with oligodendrocyte dysfunction using the AAV capsids and virus vectors of the invention.

23 Claims, 5 Drawing Sheets

Specification includes a Sequence Listing.

(56) References Cited

OTHER PUBLICATIONS

Gao et al., 2007, U.S. Appl. No. 10/423,704, i.e. U.S. Pat. No. 7,282,199 82, computer printout pp. 3-4, Gao '704.
Gray et al. "Directed Evolution of a Novel Adeno-associated Virus (AAV) Vector That Crosses the Seizure-compromised Blood-Brain Barrier (BBB)", Molecular Therapy 18(3):570-678 (2010).
Notification Concerning Transmittal of the International Preliminary Report on Patentability corresponding to International Application No. PCT/US2013/062240 mailed Apr. 9, 2015.
Notification of Transmittal of the International Search Report and the Written Opinion of the International Searching Authority, or the Declaration corresponding to International Application No. PCT/US2013/062240 mailed Jan. 16, 2014.
Office Action corresponding to Japanese Application No. 2015-534748, mailed Sep. 1, 2017.
Presentation at 15th Annual Meeting of American Society of Gene & Cell Therapy. Abstracts and Slides, May 17, 2012.
Wilson et al., 2005, N_Geneseq Accession No. ADZ27064, computer printout pp. 7-10.
Extended European Search Report corresponding to European Application No. 20178708.2 dated Oct. 14, 2020.
Office Action corresponding to Japanese Application No. 2018-151017 mailed Jun. 28, 2019.
Examination Report corresponding to Indian Application No. 2006/CHENP/2015 mailed Mar. 28, 2019.
"Office Action corresponding to Canadian Application No. 2,885,544 issued Sep. 17, 2021".
"Office Action corresponding to Canadian Application No. 2,885,544 issued Sep. 7, 2022".
Bockstael, Olivier , et al., "Recombinant AAV Delivery to the Central Nervous System", Methods in Molecular Biology 807 Chp. 7, pp. 159-177 (2011).
Fünfschilling, Ursula , et al., "Glycolytic oligodendrocytes maintain myelin and long-term axonal integrity", Nature 485:517-522 (May 24, 2012).
Hagan, Catherine E, et al., "Nervous System", Comparative Anatomy and Histology Chp. 20 pp. 339-394 (2012).
Schulz, Chris , et al., "Intraoperative Image Guidance in Neurosurgery: Development, Current Indications, and Future Trends", Radiology Research and Practice 2012:Article ID 197364, 9 pages (Feb. 20, 2012).
Stieger, Knut , et al., "Adeno-Associated Virus Mediated Gene Therapy for Retinal Degenerative Diseases", Methods in Molecular Biology 807:179-218 (2011).
Tarabishy, Ahmad B, et al., "Syndrome of Myelinated Retinal Nerve Fibers, Myopia, and Amblyopia: A Review", Surv Ophthalmol 52(6):588-596 (Nov.-Dec. 2007).
"Office Action corresponding to Chinese Application No. 202010306039.1 issued Jul. 12, 2022".
"Office Action corresponding to Chinese Application No. 202010306039.1 issued Jan. 12, 2023".
"Examination Report corresponding to European Application No. 20178708.2 dated Oct. 5, 2023".
"Office Action corresponding to Chinese Application No. 202010306039.1 issued Jul. 20, 2023".

* cited by examiner

Confocal Image of GFP-NeuN Co-localization in the Striatum

Note the lack of NeuN co-localization with the many oligodendrocytes that surround the lone NeuN positive neuron

SEQUENCE LISTING

<160> NUMBER OF SEQ ID NOS: 4

<210> SEQ ID NO 1
<211> LENGTH: 2214
<212> TYPE: DNA
<213> ORGANISM: Artificial
<220> FEATURE:
<223> OTHER INFORMATION: Chimeric AAV capsid nucleotide sequence

<400> SEQUENCE: 1

```
atggctgccg atggttatct tccagattgg ctcgaggaca ctctctctga aggaataaga        60
cagtggtgga agctcaaacc tggcccacca ccaccaaagc ccgcagagcg gcataaggac       120
gacagcaggg gtcttgtgct tcctgggtac aagtacctcg gacccttcaa cggactcgac       180
aagggagagc cggtcaacga ggcagacgcc gcggccctcg agcacgacaa agcctacgac       240
cggcagctcg acagcggaga caacccgtac ctcaagtaca ccacgccga cgcggagttt       300 caggagcgcc ttaaagaaga tacgtctttt ggggggcaacc tcgggcgagc agtcttccag       360
gccaaaaaga ggcttcttga acctcttggt ctggttgagg aagcggctaa gacggctcct       420
ggaaagaaga ggcctgtaga gcagtctcct caggaaccgg actcctcctc gggcatcggc       480
aagacaggcc agcagcccgc taaaaagaga ctcaatttcg gtcagactgg cgacacagag       540
tcagtcccag accctcaacc aatcggagaa cctcccgcag ccccctcagg tgtgggatct       600
cttacaatgg cttcaggtgg tggcgcacca gtggcagaca ataacgaagg tgccgatgga       660
gtgggtagtt cctcgggaaa ttggcattgc gattcccaat ggctggggga cagagtcatc       720
accaccagca cccgaacctg ggccctgccc acctacaaca atcacctcta caagcaaatc       780
tccaacggga catcgggagg agccaccaac gacaacacct acttcggcta cagcaccccc       840 tggggggtatt ttgactttaa cagattccac tgccactttt caccacgtga ctggcagcga       900
ctcatcaaca acaactgggg attccggccc aagagactca gcttcaagct cttcaacatc       960
caggtcaagg aggtcacgca gaatgaaggc accaagacca tcgccaataa ccttaccagc      1020
acggtccagg tcttcacgga ctcggagtac cagctgccgt acgttctcgg ctctgcccac     1080 caggggctgcc tgcctccgtt cccggcggac gtgttcatga ttccccagta cggctaccta     1140
acactcaaca acggtagtca ggccgtggga cgctcctcct tctactgcct ggaatacttt     1200
ccttcgcaga tgctgagaac cggcaacaac ttccagttta cttacacctt cgaggacgtg     1260
cctttccaca gcagctacgc ccacagccag agcttggacc ggctgatgaa tcctctgatt     1320
```

-continued

```
gaccagtacc tgtactactt gtctcggact caaacaacag gaggcacggc aaatacgcag    1380
actctgggct tcagccaagg tgggcctaat acaatggcca atcaggcaaa gaactggctg    1440
ccaggaccct gttaccgcca acaacgcgtc tcaacgacaa ccgggcaaaa caacaatagc    1500
aactttgcct ggactgctgg gaccaaatac catctgaatg gaagaaattc attggctaat    1560
cctggcatcg ctatggcaac acacaaagac gacaaggagc gttttttttcc cagtaacggg    1620 atcctgattt ttggcaaaca aaatgctgcc agagacaatg cggattacag cgatgtcatg    1680
ctcaccagcg aggaagaaat caaaaccact aaccctgtgg ctacagagga atacggtatc    1740
gtggcagata acttgcagca gcaaaacacg gctcctcaaa ttggaactgt caacagccag    1800
ggggccttac ccggtatggt ttggcagaac cgggacgtgt acctgcaggg tcccatctgg    1860
gccaagattc ctcacacgga cggcaacttc caccgtctc cgctgatggg cggctttggc    1920
ctgaaacatc ctccgcctca gatcctgatc aagaacacgc tgtacctgc ggatcctccg    1980 accaccttca accagtcaaa gctgaactct ttcatcacgc aatacagcac cggacaggtc    2040
agcgtggaaa ttgaatggga gctgcagaag gaaaacagca gcgctggaa ccccgagatc    2100 cagtacacct ccaactacta caaatctaca agtgtggact ttgctgttaa tacagaaggc    2160
gtgtactctg aaccccaccc cattggcacc cgttacctca cccgtcccct gtaa          2214
```

```
<210> SEQ ID NO 2
<211> LENGTH: 737
<212> TYPE: PRT
<213> ORGANISM: Artificial
<220> FEATURE:
<223> OTHER INFORMATION: Chimeric AAV capsid amino acid sequence

<400> SEQUENCE: 2
```

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Gly Thr Ser Gly Ala Thr Asn Asp Asn
        260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Ala Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Lys Glu Arg Phe Phe Pro Ser Asn Gly Ile Leu Ile Phe
530                 535                 540

Gly Lys Gln Asn Ala Ala Arg Asp Asn Ala Asp Tyr Ser Asp Val Met
545                 550                 555                 560

Leu Thr Ser Glu Glu Ile Lys Thr Thr Asn Pro Val Ala Thr Glu
            565                 570                 575

Glu Tyr Gly Ile Val Ala Asp Asn Leu Gln Gln Gln Asn Thr Ala Pro
        580                 585                 590

Gln Ile Gly Thr Val Asn Ser Gln Gly Ala Leu Pro Gly Met Val Trp
    595                 600                 605

Gln Asn Arg Asp Val Tyr Leu Gln Gly Pro Ile Trp Ala Lys Ile Pro
610                 615                 620

```
His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Tyr Tyr Lys Ser Thr Ser Val Asp Phe Ala Val Asn Thr Glu Gly
705                 710                 715                 720

Val Tyr Ser Glu Pro His Pro Ile Gly Thr Arg Tyr Leu Thr Arg Pro
            725                 730                 735

Leu

<210> SEQ ID NO 3
<211> LENGTH: 736
<212> TYPE: PRT
<213> ORGANISM: Artificial
<220> FEATURE:
<223> OTHER INFORMATION: Chimeric AAV capsid amino acid sequence

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240
```

-continued

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                    325                 330                 335

Leu Thr Ser Thr Val Gln Val Phe Thr Asp Ser Asp Tyr Gln Leu Pro
                    340                 345                 350

Tyr Val Leu Gly Ser Ala His Gln Gly Cys Leu Pro Pro Phe Pro Ala
                    355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                    405                 410                 415

Glu Asp Val Pro Phe His Ser Ser Tyr Ala His Ser Gln Ser Leu Asp
                    420                 425                 430

Arg Leu Met Asn Pro Leu Ile Asp Gln Tyr Leu Tyr Tyr Leu Ser Arg
            435                 440                 445

Thr Gln Thr Thr Gly Gly Thr Ala Asn Thr Gln Thr Leu Gly Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                    485                 490                 495

Asn Asn Ser Asn Phe Ala Trp Thr Ala Gly Thr Lys Tyr His Leu Asn
            500                 505                 510

Gly Arg Asn Ser Leu Ala Asn Pro Gly Ile Ala Met Ala Thr His Lys
            515                 520                 525

Asp Asp Lys Glu Arg Phe Phe Pro Ser Asn Gly Ile Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                    565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
            595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                    645                 650                 655

```
Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro His Pro Ile Gly Thr Arg Tyr Leu Thr Arg Pro Leu
                725                 730                 735

<210> SEQ ID NO 4
<211> LENGTH: 736
<212> TYPE: PRT
<213> ORGANISM: Artificial
<220> FEATURE:
<223> OTHER INFORMATION: Chimeric AAV capsid amino acid sequence

<400> SEQUENCE: 4

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Glu Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285
```

His Cys His Phe Ser Pro Arg Asp Trp Gln Arg Leu Ile Asn Asn Asn
290                 295                 300

Trp Gly Phe Arg Pro Lys Arg Leu Ser Phe Lys Leu Phe Asn Ile Gln
305                 310                 315                 320

Val Lys Glu Val Thr Asp Asn Asn Gly Val Lys Thr Ile Ala Asn Asn
            325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
            435                 440                 445

Thr Gln Thr Thr Gly Gly Thr Ala Asn Thr Gln Thr Leu Gly Phe Ser
450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Ala Asn Pro Gly Ile Ala Met Ala Thr His Lys
            515                 520                 525

Asp Asp Lys Glu Arg Phe Phe Pro Ser Asn Gly Ile Leu Ile Phe Gly
530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
            595                 600                 605

Asn Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

```
Tyr Tyr Lys Ser Thr Ser Val Asp Phe Ala Val Asn Thr Glu Gly Val
705                 710                 715                 720

Tyr Ser Glu Pro His Pro Ile Gly Thr Arg Tyr Leu Thr Arg Pro Leu
                725                 730                 735
```

AAV VECTORS TARGETED TO OLIGODENDROCYTES

STATEMENT OF PRIORITY

This application is a divisional of and claims priority to U.S. Patent Application Ser. No. 15/488,966, filed Apr. 17, 2017, which is a divisional of and claims priority to U.S. Patent Application Ser. No. 14/431,900, filed Mar. 27, 2015, now U.S. Pat. No. 9,636,370, which is a 35 U.S.C. § 371 national phase application of PCT Application No. PCT/US2013/062240, filed Sep. 27, 2013, which claims the benefit of U.S. Provisional Application Ser. No. 61/707,108, filed Sep. 28, 2012, the entire contents of each of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-637TSDV2_ST25.txt, 22,614 bytes in size, generated on Jul. 15, 2019 and filed via EFS-Web, is provided in lieu of a paper copy. The Sequence Listing is incorporated herein by reference into the specification for its disclosures.

FIELD OF THE INVENTION

The invention relates to chimeric AAV capsids targeted to oligodendrocytes, virus vectors comprising the same, and methods of using the vectors to target oligodendrocytes.

BACKGROUND OF THE INVENTION

Adeno-associated virus (AAV) was first reported to efficiently transduce muscle over ten years ago (Xiao et al., (1996) *J. Virol.* 70:8098-8108). The recombinant AAV (rAAV) genome composed of a foreign expression cassette and AAV inverted terminal repeat (ITR) sequences exists in eukaryotic cells in an episomal form that is responsible for persistent transgene expression (Schnepp et al., (2003) *J. Virol.* 77:3495-3504). AAV vectors have a good safety profile. No human disease has been associated with wild-type AAV infection and low toxicity is observed in human subjects following transduction by rAAV (Manno et al., (2003) *Blood* 101:2963-2972).

In the brain, the vast majority of AAV vectors exhibit a dominant preference for neurons with a very low efficacy for other cell types, such as oligodendrocytes. Recent advances in AAV engineering and directed evolution have expanded the ability to develop novel AAV serotypes, including vectors with altered tropism (Gray et al., (2010) *Mol. Ther.* 18:570-578). However, in the central nervous system, all AAV vectors and chimeras, except AAV4, exhibit a dominant neuronal tropism. AAV vectors that efficiently target oligodendrocytes have not been developed.

SUMMARY OF THE INVENTION

The present invention is based, in part, on the development of a chimeric AAV capsid sequence that exhibits a dominant tropism for oligodendrocytes. The chimeric capsid can be used to create AAV vectors that transduce oligodendrocytes in the central nervous system (CNS) of subjects.

Thus, one aspect of the invention relates to a nucleic acid encoding an AAV capsid, the nucleic acid comprising an AAV capsid coding sequence that is at least 90% identical to: (a) the nucleotide sequence of SEQ ID NO:1; or (b) a nucleotide sequence encoding any one of SEQ ID NOS:2-4, along with cells and viral particles comprising the nucleic acid.

Another aspect of the invention relates to an AAV capsid comprising an amino acid sequence at least 96% identical to any one of SEQ ID NOS:2-4, along with AAV particles comprising an AAV vector genome and the AAV capsid of the invention.

A further aspect of the invention relates to a method of producing a recombinant AAV particle comprising an AAV capsid, the method comprising: providing a cell in vitro with a nucleic acid of the invention, an AAV rep coding sequence, an AAV vector genome comprising a heterologous nucleic acid, and helper functions for generating a productive AAV infection; and allowing assembly of the recombinant AAV particle comprising the AAV capsid and encapsidating the AAV vector genome.

An additional aspect of the invention relates to a pharmaceutical formulation comprising the nucleic acid, virus particle, AAV capsid, or AAV particle of the invention in a pharmaceutically acceptable carrier.

Another aspect of the invention relates to a method of delivering a nucleic acid of interest to an oligodendrocyte, the method comprising contacting the oligodendrocyte with the AAV particle of the invention.

A further aspect of the invention relates to a method of delivering a nucleic acid of interest to an oligodendrocyte in a mammalian subject, the method comprising administering an effective amount of the AAV particle or pharmaceutical formulation of the invention to a mammalian subject.

An additional aspect of the invention relates to a method of delivering a nucleic acid of interest to an area of the CNS bordering a compromised blood brain barrier area in a mammalian subject, the method comprising intravenously administering an effective amount of the AAV particle or pharmaceutical formulation of the invention to a mammalian subject.

Another aspect of the invention relates to a method of treating a disorder associated with oligodendrocyte dysfunction in a mammalian subject in need thereof, the method comprising administering a therapeutically effective amount of the AAV particle or pharmaceutical formulation of the invention to a mammalian subject.

A further aspect of the invention relates to a method of preparing an AAV capsid having a tropism profile of interest, the method comprising modifying the AAV capsid of the invention to insert an amino acid sequence providing the tropism profile of interest.

These and other aspects of the invention are set forth in more detail in the description of the invention below.

DETAILED DESCRIPTION OF THE INVENTION

Figure 1:
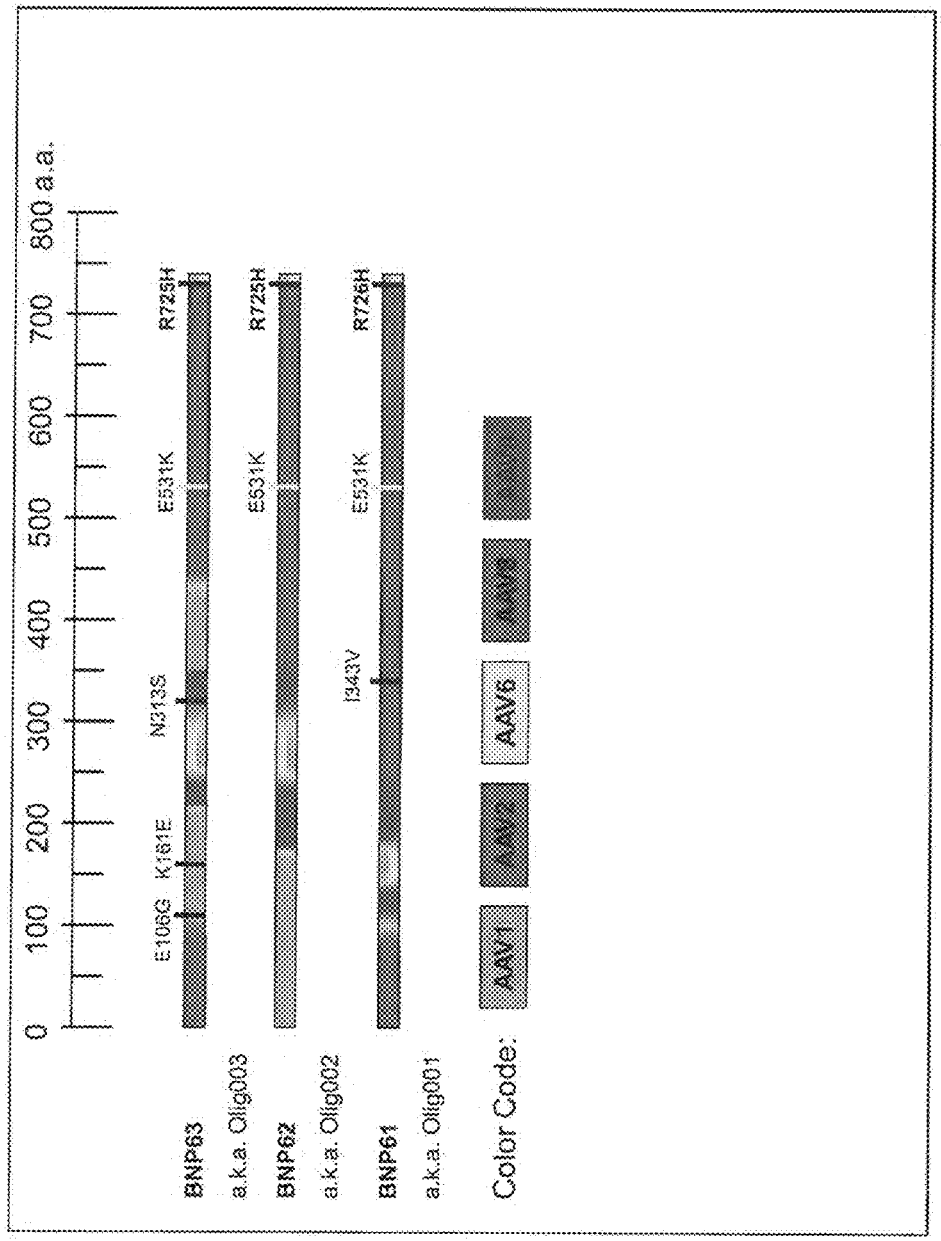
FIG. 1 shows the chimeric structure of the BNP61, BNP62, and BNP63 AAV capsid clones.

The present invention is based, in part, on the development of a chimeric AAV capsid sequence that exhibits a tropism for oligodendrocytes. The chimeric capsid can be used to create AAV vectors that transduce oligodendrocytes in the CNS of subjects.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

I. Definitions.

The designation of all amino acid positions in the AAV capsid subunits in the description of the invention and the appended claims is with respect to VP1 capsid subunit numbering.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consisting essentially of" as used herein in connection with a nucleic acid, protein or capsid structure means that the nucleic acid, protein or capsid structure does not contain any element other than the recited element(s) that significantly alters (e.g., more than about 1%, 5% or 10%) the function of interest of the nucleic acid, protein or capsid structure, e.g., tropism profile of the protein or capsid or a protein or capsid encoded by the nucleic acid.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) *J. Virol.* 78:6381-6388 and Table 1), which are also encompassed by the term "AAV."

The genomic sequences of various AAV and autonomous parvoviruses, as well as the sequences of the ITRs, Rep proteins, and capsid subunits are known in the art. Such sequences may be found in the literature or in public databases such as the GenBank® database. See, e.g., GenBank® Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivastava et al., (1983) *J. Virol.* 45:555; Chiorini et al., (1998) *J. Virol.* 71:6823; Chiorini et al., (1999) *J. Virol.* 73:1309; Bantel-Schaal et al., (1999) *J. Virol.* 73:939; Xiao et al., (1999) *J. Virol.* 73:3994;

Muramatsu et al., (1996) *Virology* 221:208; Shade et al., (1986) *J. Virol.* 58:921; Gao et al., (2002) *Proc. Nat. Acad. Sci. USA* 99:11854; international patent publications WO 00/28061, WO 99/61601, WO 98/11244; U.S. Pat. No. 6,156,303; the disclosures of which are incorporated herein in their entirety. See also Table 1. An early description of the AAV1, AAV2 and AAV3 terminal repeat sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

| Complete Genomes | GenBank Accession Number |
| --- | --- |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu 14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

A "chimeric" AAV nucleic acid capsid coding sequence or AAV capsid protein is one that combines portions of two or more capsid sequences. A "chimeric" AAV virion or particle comprises a chimeric AAV capsid protein.

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

The term "tropism profile" refers to the pattern of transduction of one or more target cells, tissues and/or organs. Representative examples of chimeric AAV capsids have a tropism profile characterized by efficient transduction of oligodendrocytes with only low transduction of neurons, astrocytes, and other CNS cells.

The term "specific for oligodendrocytes" as used herein refers to a viral vector that, when administered directly into the CNS, preferentially transduces oligodendrocytes over neurons, astrocytes, and other CNS cell types. In some embodiments, at least about 80% of the transduced cells are oligodendrocytes, e.g., at least about 85%, 90%, 95%, 96%, 97%, 98%, 99% or more oligodendrocytes.

The term "disorder associated with oligodendrocyte dysfunction" as used herein refers to a disease, disorder, or injury in which oligodendrocytes are damaged, lost, or function improperly. The term includes diseases, disorders, and injuries in which oligodendrocytes are directly affected as well as diseases, disorders, and injuries in which oligodendrocytes become dysfunctional secondary to damage to other cells (e.g., spinal cord injury).

The term "bordering a compromised blood-brain barrier area" as used herein refers to CNS cells that are adjacent to a portion of the blood-brain barrier in which the barrier function has been compromised.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism) for liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., skeletal muscle, diaphragm muscle and/or cardiac muscle).

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. The term "treat," "treats," "treating," or "treatment of" and the like also include prophylactic treatment of the subject (e.g., to prevent the onset of infection or cancer or a disorder). As used herein, the term "prevent," "prevents," or "prevention" (and grammatical equivalents thereof) are not meant to imply complete abolition of disease and encompasses any type of prophylactic treatment that reduces the incidence of the condition, delays the onset and/or progression of the condition, and/or reduces the symptoms associated with the condition. Thus, unless the context indicates otherwise, the term "treat," "treating," or "treatment of" (or grammatically equivalent terms) refer to both prophylactic and therapeutic regimens.

An "effective" or "therapeutically effective" amount as used herein is an amount that is sufficient to provide some improvement or benefit to the subject. Alternatively stated, an "effective" or "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "heterologous nucleotide sequence" or "heterologous nucleic acid" is a sequence that is not naturally occurring in the virus. Generally, the heterologous nucleic acid or nucleotide sequence comprises an open reading frame that encodes a polypeptide and/or a nontranslated RNA.

A "therapeutic polypeptide" can be a polypeptide that can alleviate or reduce symptoms that result from an absence or defect in a protein in a cell or subject. In addition, a "therapeutic polypeptide" can be a polypeptide that otherwise confers a benefit to a subject, e.g., anti-cancer effects or improvement in transplant survivability.

As used herein, the term "vector," "virus vector," "delivery vector" (and similar terms) generally refers to a virus particle that functions as a nucleic acid delivery vehicle, and which comprises the viral nucleic acid (i.e., the vector genome) packaged within the virion. Virus vectors according to the present invention comprise a chimeric AAV capsid according to the invention and can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

The AAV capsid structure is described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

II. Chimeric AAV Capsids Targeted to Oligodendrocytes.

The inventors have identified chimeric AAV capsid structures capable of preferentially transducing oligodendrocytes over neurons and other cells of the CNS. Thus, one aspect of the invention relates to a nucleic acid encoding an AAV capsid, the nucleic acid comprising, consisting essentially of, or consisting of an AAV capsid coding sequence that is at least 90% identical to: (a) the nucleotide sequence of SEQ ID NO:1; or (b) a nucleotide sequence encoding SEQ ID NO:2; and viruses comprising the chimeric AAV capsids. In some embodiments, the AAV capsid coding sequence is at least 91%, 92%, 93%, 94%, 95%, 96%, 97%, 98% or 99% identical to the nucleotide sequence of (a) or (b). In another embodiment, the AAV capsid coding sequence comprises, consist essentially of, or consist of the nucleotide sequence of (a) or (b).

```
AAV Capside Nucleotide Sequence of BNP61
                                                        (SEQ ID NO: 1)
            atggctgccg atggttatct tccagattgg ctcgaggaca ctctctctga     50
aggaataaga cagtggtgga agctcaaacc tggcccacca ccaccaaagc    100
ccgcagagcg gcataaggac gacagcaggg gtcttgtgct tcctgggtac    150
aagtacctcg gacccttcaa cggactcgac aagggagagc cggtcaacga    200
ggcagacgcc gcggccctcg agcacgacaa agcctacgac cggcagctcg    250
acagcggaga caacccgtac ctcaagtaca accacgccga cgcggagttt    300
caggagcgcc ttaaagaaga tacgtctttt ggggggcaacc tcgggcgagc    350 agtcttccag gccaaaaaga ggcttcttga acctcttggt ctggttgagg    400
aagcggctaa gacggctcct ggaaagaaga ggcctgtaga gcagtctcct    450
caggaaccgg actcctcctc gggcatcggc aagacaggcc agcagcccgc    500
taaaaagaga ctcaatttcg gtcagactgg cgacacagag tcagtcccag    550
accctcaacc aatcggagaa cctcccgcag cccctcagg tgtgggatct    600 cttacaatgg cttcaggtgg tggcgcacca gtggcagaca ataacgaagg    650
tgccgatgga gtgggtagtt cctcgggaaa ttggcattgc gattcccaat    700
ggctggggga cagagtcatc accaccagca cccgaacctg ggccctgccc    750
```

-continued

```
acctacaaca atcacctcta caagcaaatc tccaacggga catcgggagg  800
agccaccaac gacaacacct acttcggcta cagcaccccc tggggtatt   850
ttgactttaa cagattccac tgccactttt caccacgtga ctggcagcga  900
ctcatcaaca caactgggga ttccggcccc aagagactca gcttcaagct  950
cttcaacatc caggtcaagg aggtcacgca gaatgaaggc accaagacca 1000
tcgccaataa ccttaccagc acggtccagg tcttcacgga ctcggagtac 1050
cagctgccgt acgttctcgg ctctgcccac cagggctgcc tgcctccgtt 1100
cccggcggac gtgttcatga ttccccagta cggctaccta acactcaaca 1150
acggtagtca ggccgtggga cgctcctcct tctactgcct ggaatacttt 1200
ccttcgcaga tgctgagaac cggcaacaac ttccagttta cttacacctt 1250
cgaggacgtg cctttccaca gcagctacgc ccacagccag agcttggacc 1300
ggctgatgaa tcctctgatt gaccagtacc tgtactactt gtctcggact 1350
caaacaacag gaggcacggc aaatacgcag actctgggct cagccaagg  1400
tgggcctaat acaatggcca atcaggcaaa gaactgctg ccaggaccct  1450
gttaccgcca acaacgcgtc tcaacgacaa ccgggcaaaa caacaatagc 1500
aactttgcct ggactgctgg gaccaaatac catctgaatg gaagaaattc 1550
attggctaat cctggcatcg ctatggcaac acacaaagac gacaaggagc 1600
gttttttttcc cagtaacggg atcctgattt ttggcaaaca aaatgctgcc 1650
agagacaatg cggattacag cgatgtcatg ctcaccagcg aggaagaaat 1700
caaaaccact aaccctgtgg ctacagagga atacggtatc gtggcagata 1750
acttgcagca gcaaaacacg gctcctcaaa ttggaactgt caacagccag 1800
ggggccttac ccggtatggt ttggcagaac cgggacgtgt acctgcaggg 1850
tcccatctgg gccaagattc ctcacacgga cggcaacttc cacccgtctc 1900
cgctgatggg cggctttggc ctgaaacatc ctccgcctca gatcctgatc 1950
aagaacacgc tgtacctgc ggatcctccg accaccttca accagtcaaa 2000
gctgaactct ttcatcacgc aatacagcac cggacaggtc agcgtggaaa 2050
ttgaatggga gctgcagaag gaaaacagca agcgctggaa ccccgagatc 2100
cagtacacct ccaactacta caaatctaca agtgtggact tgctgttaa  2150
tacagaaggc gtgtactctg aaccccaccc cattggcacc cgttacctca 2200
cccgtccct gtaa
```

AAV Capsid Amino Acid Sequence of BNP61

(SEQ ID NO: 2)

```
MAADGYLPDW LEDTLSEGIR QWWKLKPGPP PPKPAERHKD DSRGLVLPGY  50
KYLGPFNGLD KGEPVNEADA AALEHDKAYD RQLDSGDNPY LKYNHADAEF 100
QERLKEDTSF GGNLGRAVFQ AKKRLLEPLG LVEEAAKTAP GKKRPVEQSP 150
QEPDSSSGIG KTGQQPAKKR LNFGQTGDTE SVPDPQPIGE PPAAPSGVGS 200
LTMASGGGAP VADNNEGADG VGSSSGNWHC DSQWLGDRVI TTSTRTWALP 250
TYNNHLYKQI SNGTSGGATN DNTYFGYSTP WGYFDFNRFH CHFSPRDWQR 300
LINNNWGFRP KRLSFKLFNI QVKEVTQNEG TKTIANNLTS TVQVFTDSEY 350
QLPYVLGSAH QGCLPPFPAD VFMIPQYGYL TLNNGSQAVG RSSFYCLEYF 400
PSQMLRTGNN FQFTYTFEDV PFHSSYAHSQ SLDRLMNPLI DQYLYYLSRT 450
```

```
QTTGGTANTQ TLGFSQGGPN TMANQAKNWL PGPCYRQQRV STTTGQNNNS    500

NFAWTAGTKY HLNGRNSLAN PGIAMATHKD DKERFFPSNG ILIFGKQNAA    550

RDNADYSDVM LTSEEEIKTT NPVATEEYGI VADNLQQQNT APQIGTVNSQ    600

GALPGMVWQN RDVYLQGPIW AKIPHTDGNF HPSPLMGGFG LKHPPPQILI    650

KNIPVPADPP TTFNQSKLNS FITQYSTGQV SVEIEWELQK ENSKRWNPEI    700

QYTSNYYKST SVDFAVNTEG VYSEPHPIGT RYLTRPL
```

In some embodiments, the nucleic acid encoding an AAV capsid comprises, consists essentially of, or consists of an AAV capsid coding sequence that is at least 90% identical to a nucleotide sequence encoding SEQ ID NOS:3 or 4; and viruses comprising the chimeric AAV capsids. In some embodiments, the AAV capsid coding sequence is at least 91%, 92%, 93%, 94%, 95%, 96%, 97%, 98% or 99% identical to the nucleotide sequence encoding SEQ ID NOS:3 or 4. In another embodiment, the AAV capsid coding sequence comprises, consists essentially of, or consists of the nucleotide sequence encoding SEQ ID NOS:3 or 4.

```
AAV Capsid Amino Acid Sequence of BNP62
                                                  (SEQ ID NO: 3)
           MAADGYLPDW LEDNLSEGIR EWWDLKPGAP KPKANQQKQD DGRGLVLPGY     50

KYLGPFNGLD KGEPVNAADA AALEHDKAYD QQLKAGDNPY LRYNHADAEF    100

QERLQEDTSF GGNLGRAVFQ AKKRVLEPLG LVEEGAKTAP GKKRPVEQSP    150

QEPDSSSGIG KTGQQPAKKR LNFGQTGDTE SVPDPQPIGE PPAAPSGVGS    200

LTMASGGGAP VADNNEGADG VGSSSGNWHC DSQWLGDRVI TTSTRTWALP    250

TYNNHLYKQI SSASTGASND NHYFGYSTPW GYFDFNRFHC HFSPRDWQRL    300

INNNWGFRPK RLNFKLFNIQ VKEVTDNNGV KTIANNLTST VQVFTDSDYQ    350

LPYVLGSAHQ GCLPPFPADV FMIPQYGYLT LNNGSQAVGR SSFYCLEYFP    400

SQMLRTGNNF QFTYTFEDVP FHSSYAHSQS LDRLMNPLID QYLYYLSRTQ    450

TTGGTANTQT LGFSQGGPNT MANQAKNWLP GPCYRQQRVS TTTGQNNNSN    500

FAWTAGTKYH LNGRNSLANP GIAMATHKDD KERFFPSNGI LIFGKQNAAR    550

DNADYSDVML TSEEEIKTTN PVATEEYGIV ADNLQQQNTA PQIGTVNSQG    600

ALPGMVWQNR DVYLQGPIWA KIPHTDGNFH PSPLMGGFGL KHPPPQILIK    650

NTPVPADPPT TFNQSKLNSF ITQYSTGQVS VEIEWELQKE NSKRWNPEIQ    700

YTSNYYKSTS VDFAVNTEGV YSEPHPIGTR YLTRPL

AAV Capsid Amino Acid Sequence of BNP63
                                                  (SEQ ID NO: 4)
           MAADGYLPDW LEDTLSEGIR QWWKLKPGPP PPKPAERHKD DSRGLVLPGY     50

KYLGPFNGLD KGEPVNEADA AALEHDKAYD RQLDSGDNPY LKYNHADAEF    100

QERLQGDTSF GGNLGRAVFQ AKKRVLEPLG LVEEGAKTAP GKKRPVEQSP    150

QEPDSSSGIG ETGQQPAKKR LNFGQTGDSE SVPDPQPLGE PPATPAAVGP    200

TTMASGGGAP MADNNEGADG VGSSSGNWHC DSQWLGDRVI TTSTRTWALP    250

TYNNHLYKQI SSASTGASND NHYFGYSTPW GYFDFNRFHC HFSPRDWQRL    300

INNNWGFRPK RLSFKLFNIQ VKEVTDNNGV KTIANNLTST VQVFTDSEYQ    350

LPYVLGSAHQ GCLPPFPADV FMIPQYGYLT LNNGSQAVGR SSFYCLEYFP    400

SQMLRTGNNF TFSYTFEDVP FHSSYAHSQS LDRLMNPLID QYLYYLSRTQ    450

TTGGTANTQT LGFSQGGPNT MANQAKNWLP GPCYRQQRVS TTTGQNNNSN    500

FAWTAGTKYH LNGRNSLANP GIAMATHKDD KERFFPSNGI LIFGKQNAAR    550

DNADYSDVML TSEEEIKTTN PVATEEYGIV ADNLQQQNTA PQIGTVNSQG    600
```

```
                             -continued
ALPGMVWQNR DVYLQGPIWA KIPHTDGNFH PSPLMGGFGL KHPPPQILIK    650

NTPVPADPPT TFNQSKLNSF ITQYSTGQVS VEIEWELQKE NSKRWNPEIQ    700

YTSNYYKSTS VDFAVNTEGV YSEPHPIGTR YLTRPL
```

SEQ ID NOS:2-4 show examples of the VP1 capsid protein sequences of the invention. The designation of all amino acid positions in the description of the invention and the appended claims is with respect to VP1 numbering. Those skilled in the art will understand that the AAV capsid generally contains the smaller VP2 and VP3 capsid proteins as well. Due to the overlap of the coding sequences for the AAV capsid proteins, the nucleic acid coding sequences and amino acid sequences of the VP2 and VP3 capsid proteins will be apparent from the VP1 sequences shown in SEQ ID NOS:1-4. In particular, VP2 starts at nucleotide 412 (acg) of SEQ ID NO:1 and threonine 148 of SEQ ID NO:2. VP3 starts at nucleotide 607 (atg) of SEQ ID NO:1 and methionine 203 of SEQ ID NO:2. In certain embodiments, isolated VP2 and VP3 capsid proteins comprising the sequence from SEQ ID NOS:2-4 and isolated nucleic acids encoding the VP2 or VP3 proteins, or both, are contemplated.

The invention also provides chimeric AAV capsid proteins and chimeric capsids, wherein the capsid protein comprises, consists essentially of, or consists of an amino acid sequence as shown in one of SEQ ID NOS:2-4, wherein 1, 2 or fewer, 3 or fewer, 4 or fewer, 5 or fewer, 6 or fewer, 7 or fewer, 8 or fewer, 9 or fewer, 10 or fewer, 12 or fewer, 15 or fewer, 20 or fewer, 25 or fewer, 30 or fewer, 40 or fewer, or 50 or fewer of the amino acids within the capsid protein coding sequence of one of SEQ ID NOS:2-4 is substituted by another amino acid (naturally occurring, modified and/or synthetic), optionally a conservative amino acid substitution, and/or are deleted and/or there are insertions (including N-terminal and C-terminal extensions) of 1, 2 or fewer, 3 or fewer, 4 or fewer, 5 or fewer, 6 or fewer, 7 or fewer, 8 or fewer, 9 or fewer, 10 or fewer, 12 or fewer, 15 or fewer, 20 or fewer, 25 or fewer, 30 or fewer, 40 or fewer, or 50 or fewer amino acids or any combination of substitutions, deletions and/or insertions, wherein the substitutions, deletions and/or insertions do not unduly impair the structure and/or function of a virion (e.g., an AAV virion) comprising the variant capsid protein or capsid. For example, in representative embodiments of the invention, an AAV virion comprising the chimeric capsid protein substantially retains at least one property of a chimeric virion comprising a chimeric capsid protein as shown in one of SEQ ID NOS:2-4. For example, the virion comprising the chimeric capsid protein can substantially retain the oligodendrocyte tropism profile of a virion comprising the chimeric AAV capsid protein as shown in one of SEQ ID NOS:2-4. Methods of evaluating biological properties such as virus transduction are well-known in the art (see, e.g., the Examples).

Conservative amino acid substitutions are known in the art. In particular embodiments, a conservative amino acid substitution includes substitutions within one or more of the following groups: glycine, alanine; valine, isoleucine, leucine; aspartic acid, glutamic acid; asparagine, glutamine; serine, threonine; lysine, arginine; and/or phenylalanine, tyrosine.

It will be apparent to those skilled in the art that the amino acid sequences of the chimeric AAV capsid protein of SEQ ID NOS:2-4 can further be modified to incorporate other modifications as known in the art to impart desired properties. As nonlimiting possibilities, the capsid protein can be modified to incorporate targeting sequences (e.g., RGD) or sequences that facilitate purification and/or detection. For example, the capsid protein can be fused to all or a portion of glutathione-S-transferase, maltose-binding protein, a heparin/heparan sulfate binding domain, poly-His, a ligand, and/or a reporter protein (e.g., Green Fluorescent Protein, β-glucuronidase, β-galactosidase, luciferase, etc.), an immunoglobulin Fc fragment, a single-chain antibody, hemagglutinin, c-myc, FLAG epitope, and the like to form a fusion protein. Methods of inserting targeting peptides into the AAV capsid are known in the art (see, e.g., international patent publication WO 00/28004; Nicklin et al., (2001) Mol. Ther. 474-181; White et al., (2004) Circulation 109:513-319; Muller et al., (2003) Nature Biotech. 21:1040-1046.

The viruses of the invention can further comprise a duplexed viral genome as described in international patent publication WO 01/92551 and U.S. Pat. No. 7,465,583.

The invention also provides AAV capsids comprising the chimeric AAV capsid proteins of the invention and virus particles (i.e., virions) comprising the same, wherein the virus particle packages (i.e., encapsidates) a vector genome, optionally an AAV vector genome. In particular embodiments, the invention provides an AAV particle comprising an AAV capsid comprising an AAV capsid protein of the invention, wherein the AAV capsid packages an AAV vector genome. The invention also provides an AAV particle comprising an AAV capsid or AAV capsid protein encoded by the chimeric nucleic acid capsid coding sequences of the invention.

In particular embodiments, the virion is a recombinant vector comprising a heterologous nucleic acid of interest, e.g., for delivery to a cell. Thus, the present invention is useful for the delivery of nucleic acids to cells in vitro, ex vivo, and in vivo. In representative embodiments, the recombinant vector of the invention can be advantageously employed to deliver or transfer nucleic acids to animal (e.g., mammalian) cells.

Any heterologous nucleotide sequence(s) may be delivered by a virus vector of the present invention. Nucleic acids of interest include nucleic acids encoding polypeptides, optionally therapeutic (e.g., for medical or veterinary uses) and/or immunogenic (e.g., for vaccines) polypeptides.

In some embodiments, the polypeptide is one that stimulates growth and/or differentiation of oligodendrocytes. Examples include, without limitation, insulin-like growth factor-1, glial-derived neurotrophic factor, neurotrophin-3, artemin, transforming growth factor alpha, platelet-derived growth factor, leukemia inhibitory factor, prolactin, monocarboxylate transporter 1, or nuclear factor 1A.

Therapeutic polypeptides include, but are not limited to, cystic fibrosis transmembrane regulator protein (CFTR), dystrophin (including the protein product of dystrophin mini-genes or micro-genes, see, e.g., Vincent et al., (1993) Nature Genetics 5:130; U.S. Patent Publication No. 2003017131; Wang et al., (2000) Proc. Natl. Acad. Sci. USA 97:13714-9 [mini-dystrophin]; Harper et al., (2002) Nature Med. 8:253-61 [micro-dystrophin]); mini-agrin, a laminin-α2, a sarcoglycan (α, ≠2, γ Or δ), Fukutin-related protein, myostatin pro-peptide, follistatin, dominant negative myostatin, an angiogenic factor (e.g., VEGF, angiopoietin-1 or 2), an anti-apoptotic factor (e.g., heme-oxygenase-1, TGF-β, inhibitors of pro-apoptotic signals such as caspases, proteases, kinases, death receptors [e.g., CD-095], modulators of cytochrome C release, inhibitors of mitochondrial pore opening and swelling); activin type II soluble receptor, anti-inflammatory polypeptides such as the Ikappa B dominant mutant, sarcospan, utrophin, mini-utrophin, antibodies or antibody fragments against myostatin or myostatin propeptide, cell cycle modulators, Rho kinase modulators such as Cethrin, which is a modified bacterial C3 exoenzyme [available from BioAxone Therapeutics, Inc., Saint-Lauren, Quebec, Canada], BCL-xL, BCL2, XIAP, FLICEc-s, dominant-negative caspase-8, dominant negative caspase-9, SPI-6 (see, e.g., U.S. Patent Application No. 20070026076), transcriptional factor PGC-α1, Pinch gene, ILK gene and thymosin β4 gene), clotting factors (e.g., Factor VIII, Factor IX, Factor X, etc.), erythropoietin, angiostatin, endostatin, catalase, tyrosine hydroxylase, an intracellular and/or extracellular superoxide dismutase, leptin, the LDL receptor, neprilysin, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, a cytokine (e.g., α-interferon, β-interferon, interferon-γ, interleukins-1 through -14, granulocyte-macrophage colony stimulating factor, lymphotoxin, and the like), peptide growth factors, neurotrophic factors and hormones (e.g., somatotropin, insulin, insulin-like growth factors including IGF-1 and IGF-2, GLP-1, platelet derived growth factor, epidermal growth factor, fibroblast growth factor, nerve growth factor, neurotrophic factor –3 and –4, brain-derived neurotrophic factor, glial derived growth factor, transforming growth factor –α and –β, and the like), bone morphogenic proteins (including RANKL and VEGF), a lysosomal protein, a glutamate receptor, a lymphokine, soluble CD4, an Fc receptor, a T cell receptor, ApoE, ApoC, inhibitor 1 of protein phosphatase inhibitor 1 (I-1), phospholamban, serca2a, lysosomal acid α-glucosidase, α-galactosidase A, Barkct, β2-adrenergic receptor, β2-adrenergic receptor kinase (BARK), phosphoinositide-3 kinase (PI3 kinase), calsarcin, a receptor (e.g., the tumor necrosis growth factor-α soluble receptor), an anti-inflammatory factor such as IRAP, Pim-1, PGC-1α, SOD-1, SOD-2, ECF-SOD, kallikrein, thymosin-β4, hypoxia-inducible transcription factor [HIF], an angiogenic factor, S100A1, parvalbumin, adenylyl cyclase type 6, a molecule that effects G-protein coupled receptor kinase type 2 knockdown such as a truncated constitutively active bARKct; phospholamban inhibitory or dominant-negative molecules such as phospholamban S16E, a monoclonal antibody (including single chain monoclonal antibodies) or a suicide gene product (e.g., thymidine kinase, cytosine deaminase, diphtheria toxin, and tumor necrosis factors such as TNF-α), and any other polypeptide that has a therapeutic effect in a subject in need thereof.

Heterologous nucleotide sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase.

Alternatively, the heterologous nucleic acid may encode an antisense oligonucleotide, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including small interfering RNAs (siRNA) that mediate gene silencing (see, Sharp et al., (2000) *Science* 287:2431), microRNA, or other non-translated "functional" RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi or antisense RNA against the multiple drug resistance (MDR) gene product (e.g., to treat tumors and/or for administration to the heart to prevent damage by chemotherapy), RNAi or antisense RNA against myostatin (Duchenne or Becker muscular dystrophy), RNAi or antisense RNA against VEGF or a tumor immunogen including but not limited to those tumor immunogens specifically described herein (to treat tumors), RNAi or antisense oligonucleotides targeting mutated dystrophins (Duchenne or Becker muscular dystrophy), RNAi or antisense RNA against the hepatitis B surface antigen gene (to prevent and/or treat hepatitis B infection), RNAi or antisense RNA against the HIV tat and/or rev genes (to prevent and/or treat HIV) and/or RNAi or antisense RNA against any other immunogen from a pathogen (to protect a subject from the pathogen) or a defective gene product (to prevent or treat disease). RNAi or antisense RNA against the targets described above or any other target can also be employed as a research reagent.

As is known in the art, anti-sense nucleic acids (e.g., DNA or RNA) and inhibitory RNA (e.g., microRNA and RNAi such as siRNA or shRNA) sequences can be used to induce "exon skipping" in patients with muscular dystrophy arising from defects in the dystrophin gene. Thus, the heterologous nucleic acid can encode an antisense nucleic acid or inhibitory RNA that induces appropriate exon skipping. Those skilled in the art will appreciate that the particular approach to exon skipping depends upon the nature of the underlying defect in the dystrophin gene, and numerous such strategies are known in the art. Exemplary antisense nucleic acids and inhibitory RNA sequences target the upstream branch point and/or downstream donor splice site and/or internal splicing enhancer sequence of one or more of the dystrophin exons (e.g., exons 19 or 23). For example, in particular embodiments, the heterologous nucleic acid encodes an antisense nucleic acid or inhibitory RNA directed against the upstream branch point and downstream splice donor site of exon 19 or 23 of the dystrophin gene. Such sequences can be incorporated into an AAV vector delivering a modified U7 snRNA and the antisense nucleic acid or inhibitory RNA (see, e.g., Goyenvalle et al., (2004) *Science* 306:1796-1799). As another strategy, a modified U1 snRNA can be incorporated into an AAV vector along with siRNA, microRNA or antisense RNA complementary to the upstream and downstream splice sites of a dystrophin exon (e.g., exon 19 or 23) (see, e.g., Denti et al., (2006) *Proc. Nat. Acad. Sci. USA* 103: 3758-3763). Further, antisense nucleic acids and inhibitory RNA can target the splicing enhancer sequences within exons 19, 43, 45 or 53 (see, e.g., U.S. Pat. Nos. 6,653,467; 6,727,355; and U.S. Pat. No. 6,653,466).

Ribozymes are RNA-protein complexes that cleave nucleic acids in a site-specific fashion. Ribozymes have specific catalytic domains that possess endonuclease activity (Kim et al., (1987) *Proc. Natl. Acad. Sci. USA* 84:8788; Gerlach et al., (1987) *Nature* 328:802; Forster and Symons, (1987) *Cell* 49:211). For example, a large number of ribozymes accelerate phosphoester transfer reactions with a high degree of specificity, often cleaving only one of several phosphoesters in an oligonucleotide substrate (Michel and Westhof, (1990) *J. Mol. Biol.* 216:585; Reinhold-Hurek and Shub, (1992) *Nature* 357:173). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, (1989) *Nature* 338:217). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of nucleic acid expression may be particularly suited to therapeutic applications (Scanlon et al., (1991) *Proc. Natl. Acad. Sci. USA* 88:10591; Sarver et al., (1990) *Science* 247:1222; Sioud et al., (1992) *J. Mol. Biol.* 223:831).

MicroRNAs (mir) are natural cellular RNA molecules that can regulate the expression of multiple genes by controlling the stability of the mRNA. Over-expression or diminution of a particular microRNA can be used to treat a dysfunction and has been shown to be effective in a number of disease states and animal models of disease (see, e.g., Couzin, (2008) *Science* 319:1782-4). The chimeric AAV can be used to deliver microRNA into cells, tissues and subjects for the treatment of genetic and acquired diseases, or to enhance functionality and promote growth of certain tissues. For example, mir-1, mir-133, mir-206 and/or mir-208 can be used to treat cardiac and skeletal muscle disease (see, e.g., Chen et al., (2006) *Genet.* 38:228-33; van Rooij et al., (2008) *Trends Genet.* 24:159-66). MicroRNA can also be used to modulate the immune system after gene delivery (Brown et al., (2007) *Blood* 110:4144-52).

The term "antisense oligonucleotide" (including "antisense RNA") as used herein, refers to a nucleic acid that is complementary to and specifically hybridizes to a specified DNA or RNA sequence. Antisense oligonucleotides and nucleic acids that encode the same can be made in accordance with conventional techniques. See, e.g., U.S. Pat. No. 5,023,243 to Tullis; U.S. Pat. No. 5,149,797 to Pederson et al.

Those skilled in the art will appreciate that it is not necessary that the antisense oligonucleotide be fully complementary to the target sequence as long as the degree of sequence similarity is sufficient for the antisense nucleotide sequence to specifically hybridize to its target (as defined above) and reduce production of the protein product (e.g., by at least about 30%, 40%, 50%, 60%, 70%, 80%, 90%, 95% or more).

To determine the specificity of hybridization, hybridization of such oligonucleotides to target sequences can be carried out under conditions of reduced stringency, medium stringency or even stringent conditions. Suitable conditions for achieving reduced, medium and stringent hybridization conditions are as described herein.

Alternatively stated, in particular embodiments, antisense oligonucleotides of the invention have at least about 60%, 70%, 80%, 90%, 95%, 97%, 98% or higher sequence identity with the complement of the target sequence and reduce production of the protein product (as defined above). In some embodiments, the antisense sequence contains 1, 2, 3, 4, 5, 6, 7, 8, 9 or 10 mismatches as compared with the target sequence.

Methods of determining percent identity of nucleic acid sequences are described in more detail elsewhere herein.

The length of the antisense oligonucleotide is not critical as long as it specifically hybridizes to the intended target and reduces production of the protein product (as defined above) and can be determined in accordance with routine procedures. In general, the antisense oligonucleotide is at least about eight, ten or twelve or fifteen nucleotides in length and/or less than about 20, 30, 40, 50, 60, 70, 80, 100 or 150 nucleotides in length.

RNA interference (RNAi) is another useful approach for reducing production of a protein product (e.g., shRNA or siRNA). RNAi is a mechanism of post-transcriptional gene silencing in which double-stranded RNA (dsRNA) corresponding to a target sequence of interest is introduced into a cell or an organism, resulting in degradation of the corresponding mRNA. The mechanism by which RNAi achieves gene silencing has been reviewed in Sharp et al., (2001) *Genes Dev* 15: 485-490; and Hammond et al., (2001) *Nature Rev. Gen.* 2:110-119). The RNAi effect persists for multiple cell divisions before gene expression is regained. RNAi is therefore a powerful method for making targeted knockouts or "knockdowns" at the RNA level. RNAi has proven successful in human cells, including human embryonic kidney and HeLa cells (see, e.g., Elbashir et al., *Nature* (2001) 411:494-8).

Initial attempts to use RNAi in mammalian cells resulted in antiviral defense mechanisms involving PKR in response to the dsRNA molecules (see, e.g., Gil et al., (2000) *Apoptosis* 5:107). It has since been demonstrated that short synthetic dsRNA of about 21 nucleotides, known as "short interfering RNAs" (siRNA) can mediate silencing in mammalian cells without triggering the antiviral response (see, e.g., Elbashir et al., *Nature* (2001) 411:494-8; Caplen et al., (2001) *Proc. Nat. Acad. Sci. USA* 98:9742).

The RNAi molecule (including an siRNA molecule) can be a short hairpin RNA (shRNA; see Paddison et al., (2002), *Proc. Nat. Acad. Sci. USA* 99:1443-1448), which is believed to be processed in the cell by the action of the RNase III like enzyme Dicer into 20-25 mer siRNA molecules. The shRNAs generally have a stem-loop structure in which two inverted repeat sequences are separated by a short spacer sequence that loops out. There have been reports of shRNAs with loops ranging from 3 to 23 nucleotides in length. The loop sequence is generally not critical. Exemplary loop sequences include the following motifs: AUG, CCC, UUCG, CCACC, CTCGAG, AAGCUU, CCACACC and UUCAAGAGA.

The RNAi can further comprise a circular molecule comprising sense and antisense regions with two loop regions on either side to form a "dumbbell" shaped structure upon dsRNA formation between the sense and antisense regions. This molecule can be processed in vitro or in vivo to release the dsRNA portion, e.g., a siRNA.

International patent publication WO 01/77350 describes a vector for bi-directional transcription to generate both sense and antisense transcripts of a heterologous sequence in a eukaryotic cell. This technique can be employed to produce RNAi for use according to the invention.

Shinagawa et al., (2003) *Genes Dev.* 17:1340 reported a method of expressing long dsRNAs from a CMV promoter (a pol II promoter), which method is also applicable to tissue specific pol II promoters. Likewise, the approach of Xia et al., (2002) *Nature Biotech.* 20:1006, avoids poly(A) tailing and can be used in connection with tissue-specific promoters.

Methods of generating RNAi include chemical synthesis, in vitro transcription, digestion of long dsRNA by Dicer (in vitro or in vivo), expression in vivo from a delivery vector, and expression in vivo from a PCR-derived RNAi expression cassette (see, e.g., TechNotes 10(3) "Five Ways to Produce siRNAs," from Ambion, Inc., Austin, TX; available at www.ambion.com).

Guidelines for designing siRNA molecules are available (see e.g., literature from Ambion, Inc., Austin, TX; available at www.ambion.com). In particular embodiments, the siRNA sequence has about 30-50% G/C content. Further, long stretches of greater than four T or A residues are generally avoided if RNA polymerase III is used to transcribe the RNA. Online siRNA target finders are available, e.g., from Ambion, Inc. (www.ambion.com), through the Whitehead Institute of Biomedical Research (www.jura.wi.mit.edu) or from Dharmacon Research, Inc. (www.dharmacon.com).

The antisense region of the RNAi molecule can be completely complementary to the target sequence, but need not be as long as it specifically hybridizes to the target sequence (as defined above) and reduces production of the protein product (e.g., by at least about 30%, 40%, 50%, 60%, 70%, 80%, 90%, 95% or more). In some embodiments, hybridization of such oligonucleotides to target sequences can be carried out under conditions of reduced stringency, medium stringency or even stringent conditions, as defined above.

In other embodiments, the antisense region of the RNAi has at least about 60%, 70%, 80%, 90%, 95%, 97%, 98% or higher sequence identity with the complement of the target sequence and reduces production of the protein product (e.g., by at least about 30%, 40%, 50%, 60%, 70%, 80%, 90%, 95% or more). In some embodiments, the antisense region contains 1, 2, 3, 4, 5, 6, 7, 8, 9 or 10 mismatches as compared with the target sequence. Mismatches are generally tolerated better at the ends of the dsRNA than in the center portion.

In particular embodiments, the RNAi is formed by intermolecular complexing between two separate sense and antisense molecules. The RNAi comprises a double stranded region formed by the intermolecular basepairing between the two separate strands. In other embodiments, the RNAi comprises a ds region formed by intramolecular basepairing within a single nucleic acid molecule comprising both sense and antisense regions, typically as an inverted repeat (e.g., a shRNA or other stem loop structure, or a circular RNAi molecule). The RNAi can further comprise a spacer region between the sense and antisense regions.

Generally, RNAi molecules are highly selective. If desired, those skilled in the art can readily eliminate candidate RNAi that are likely to interfere with expression of nucleic acids other than the target by searching relevant databases to identify RNAi sequences that do not have substantial sequence homology with other known sequences, for example, using BLAST (available at www.ncbi.nlm.nih.gov/BLAST).

Kits for the production of RNAi are commercially available, e.g., from New England Biolabs, Inc. and Ambion, Inc.

The recombinant virus vector may also comprise a heterologous nucleotide sequence that shares homology with and recombines with a locus on the host chromosome. This approach may be utilized to correct a genetic defect in the host cell.

The present invention also provides recombinant virus vectors that express an immunogenic polypeptide, e.g., for vaccination. The heterologous nucleic acid may encode any immunogen of interest known in the art including, but are not limited to, immunogens from human immunodeficiency virus, influenza virus, gag proteins, tumor antigens, cancer antigens, bacterial antigens, viral antigens, and the like.

Alternatively, the immunogen can be presented in the virus capsid (e.g., incorporated therein) or tethered to the virus capsid (e.g., by covalent modification).

The use of parvoviruses as vaccines is known in the art (see, e.g., Miyamura et al., (1994) *Proc. Nat. Acad. Sci. USA* 91:8507; U.S. Pat. No. 5,916,563 to Young et al., 5,905,040 to Mazzara et al., U.S. Pat. Nos. 5,882,652, 5,863,541 to Samulski et al.; the disclosures of which are incorporated herein in their entireties by reference). The antigen may be presented in the virus capsid. Alternatively, the antigen may be expressed from a heterologous nucleic acid introduced into a recombinant vector genome.

An immunogenic polypeptide, or immunogen, may be any polypeptide suitable for protecting the subject against a disease, including but not limited to microbial, bacterial, protozoal, parasitic, fungal and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen, or a severe acute respiratory syndrome (SARS) immunogen such as a S [S1 or S2], M, E, or N protein or an immunogenic fragment thereof). The immunogen may further be a polio immunogen, herpes immunogen (e.g., CMV, EBV, HSV immunogens) mumps immunogen, measles immunogen, rubella immunogen, diphtheria toxin or other diphtheria immunogen, pertussis antigen, hepatitis (e.g., hepatitis A, hepatitis B or hepatitis C) immunogen, or any other vaccine immunogen known in the art.

Alternatively, the immunogen may be any tumor or cancer cell antigen. Optionally, the tumor or cancer antigen is expressed on the surface of the cancer cell. Exemplary cancer and tumor cell antigens are described in S. A. Rosenberg, (1999) *Immunity* 10:281). Illustrative cancer and tumor antigens include, but are not limited to: BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124) including MART-1 (Coulie et al., (1991) *J. Exp. Med.* 180:35), gp100 (Wick et al., (1988) *J. Cutan. Pathol.* 4:201) and MAGE antigen (MAGE-1, MAGE-2 and MAGE-3) (Van der Bruggen et al., (1991) *Science,* 254: 1643), CEA, TRP-1; TRP-2; P-15 and tyrosinase (Brichard et al., (1993) *J. Exp. Med.* 178:489); HER-2/neu gene product (U.S. Pat. No. 4,968,603); CA 125; HE4; LK26; FB5 (endosialin); TAG 72; AFP; CA19-9; NSE; DU-PAN-2; CA50; Span-1; CA72-4; HCG; STN (sialyl Tn antigen); c-erbB-2 proteins; PSA; L-CanAg; estrogen receptor; milk fat globulin; p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: melanomas, adenocarcinoma, thymoma, sarcoma, lung cancer, liver cancer, colorectal cancer, non-Hodgkin's lymphoma, Hodgkin's lymphoma, leukemias, uterine cancer, breast cancer, prostate cancer, ovarian cancer, cervical cancer, bladder cancer, kidney cancer, pancreatic cancer, brain cancer, kidney cancer, stomach cancer, esophageal cancer, head and neck cancer and others (see, e.g., Rosenberg, (1996) *Annu. Rev. Med.* 47:481-91).

Alternatively, the heterologous nucleotide sequence may encode any polypeptide that is desirably produced in a cell in vitro, ex vivo, or in vivo. For example, the virus vectors may be introduced into cultured cells and the expressed protein product isolated therefrom.

It will be understood by those skilled in the art that the heterologous nucleic acid(s) of interest may be operably associated with appropriate control sequences. For example, the heterologous nucleic acid may be operably associated with expression control elements, such as transcription/translation control signals, origins of replication, polyadenylation signals, internal ribosome entry sites (IRES), promoters, enhancers, and the like.

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. In one embodiment, an oligodendrocyte-specified or oligodendrocyte-preferred promoter is used. Examples include, without limitation, myelin basic protein, cyclic nucleotide phosphodiesterase, proteolipid protein, Gtx, and Sox10. Use of an oligodendrocyte-specific or preferred promoter can increase the specificity achieved by the chimeric AAV vector by further limiting expression of the heterologous nucleic acid to oligodendrocytes. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

The invention also provides chimeric AAV particles comprising an AAV capsid and an AAV genome, wherein the AAV genome "corresponds to" (i.e., encodes) the AAV capsid. Also provided are collections or libraries of such chimeric AAV particles, wherein the collection or library comprises 2 or more, 10 or more, 50 or more, 100 or more, 1000 or more, $10^4$ or more, $10^5$ or more, or $10^6$ or more distinct sequences.

The present invention further encompasses "empty" capsid particles (i.e., in the absence of a vector genome) comprising, consisting of, or consisting essentially of the chimeric AAV capsid proteins of the invention. The chimeric AAV capsids of the invention can be used as "capsid vehicles," as has been described in U.S. Pat. No. 5,863,541. Molecules that can be covalently linked, bound to or packaged by the virus capsids and transferred into a cell include DNA, RNA, a lipid, a carbohydrate, a polypeptide, a small organic molecule, or combinations of the same. Further, molecules can be associated with (e.g., "tethered to") the outside of the virus capsid for transfer of the molecules into host target cells. In one embodiment of the invention the molecule is covalently linked (i.e., conjugated or chemically coupled) to the capsid proteins. Methods of covalently linking molecules are known by those skilled in the art.

The virus capsids of the invention also find use in raising antibodies against the novel capsid structures. As a further alternative, an exogenous amino acid sequence may be inserted into the virus capsid for antigen presentation to a cell, e.g., for administration to a subject to produce an immune response to the exogenous amino acid sequence.

The invention also provides nucleic acids (e.g., isolated nucleic acids) encoding the chimeric virus capsids and chimeric capsid proteins of the invention. Further provided are vectors comprising the nucleic acids, and cells (in vivo or in culture) comprising the nucleic acids and/or vectors of the invention. Such nucleic acids, vectors and cells can be used, for example, as reagents (e.g., helper constructs or packaging cells) for the production of virus vectors as described herein.

In exemplary embodiments, the invention provides nucleic acid sequences encoding the AAV capsid of SEQ ID NOS:2-4 or at least 90% identical to the nucleotide sequence of SEQ ID NO:1. The invention also provides nucleic acids encoding the AAV capsid variants, capsid protein variants and fusion proteins as described above. In particular embodiments, the nucleic acid hybridizes to the complement of the nucleic acid sequences specifically disclosed herein under standard conditions as known by those skilled in the art and encodes a variant capsid and/or capsid protein. Optionally, the variant capsid or capsid protein substantially retains at least one property of the capsid and/or capsid or capsid protein encoded by the nucleic acid sequence of SEQ ID NO:1. For example, a virus particle comprising the variant capsid or variant capsid protein can substantially retain the oligodendrocyte tropism profile of a virus particle comprising a capsid or capsid protein encoded by a nucleic acid coding sequence of SEQ ID NO:1.

For example, hybridization of such sequences may be carried out under conditions of reduced stringency, medium stringency or even stringent conditions. Exemplary conditions for reduced, medium and stringent hybridization are as follows: (e.g., conditions represented by a wash stringency of 35-40% Formamide with 5×Denhardt's solution, 0.5% SDS and 1×SSPE at 37° C.; conditions represented by a wash stringency of 40-45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively). See, e.g., Sambrook et al., Molecular Cloning, A Laboratory Manual (2d Ed. 1989) (Cold Spring Harbor Laboratory).

In other embodiments, nucleic acid sequences encoding a variant capsid or capsid protein of the invention have at least about 90%, 91%, 92%, 93%, 94%, 95%, 96%, 97%, 98%, 99%, or higher sequence identity with the nucleic acid sequence of SEQ ID NO:1 and optionally encode a variant capsid or capsid protein that substantially retains at least one property of the capsid or capsid protein encoded by a nucleic acid of SEQ ID NO:1.

As is known in the art, a number of different programs can be used to identify whether a nucleic acid or polypeptide has sequence identity to a known sequence. Percent identity as used herein means that a nucleic acid or fragment thereof shares a specified percent identity to another nucleic acid, when optimally aligned (with appropriate nucleotide insertions or deletions) with the other nucleic acid (or its complementary strand), using BLASTN. To determine percent identity between two different nucleic acids, the percent identity is to be determined using the BLASTN program "BLAST 2 sequences". This program is available for public use from the National Center for Biotechnology Information (NCBI) over the Internet (Altschul et al., (1997) *Nucleic Acids Res.* 25(17):3389-3402). The parameters to be used are whatever combination of the following yields the highest calculated percent identity (as calculated below) with the default parameters shown in parentheses: Program—blastn Matrix—0 BLOSUM62 Reward for a match—0 or 1 (1) Penalty for a mismatch—0, −1, −2 or −3 (−2) Open gap penalty—0, 1, 2, 3, 4 or 5 (5) Extension gap penalty—0 or 1 (1) Gap x_dropoff—0 or 50 (50) Expect—10.

Percent identity or similarity when referring to polypeptides, indicates that the polypeptide in question exhibits a specified percent identity or similarity when compared with another protein or a portion thereof over the common lengths as determined using BLASTP. This program is also available for public use from the National Center for Biotechnology Information (NCBI) over the Internet (Altschul et al., (1997) *Nucleic Acids Res.* 25(17):3389-3402). Percent identity or similarity for polypeptides is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

In particular embodiments, the nucleic acid can comprise, consist essentially of, or consist of a vector including but not limited to a plasmid, phage, viral vector (e.g., AAV vector, an adenovirus vector, a herpesvirus vector, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat).

In some embodiments, the nucleic acid encoding the chimeric AAV capsid protein further comprises an AAV rep coding sequence. For example, the nucleic acid can be a helper construct for producing viral stocks.

The invention also provides packaging cells stably comprising a nucleic acid of the invention. For example, the nucleic acid can be stably incorporated into the genome of the cell or can be stably maintained in an episomal form (e.g., an "EBV based nuclear episome").

The nucleic acid can be incorporated into a delivery vector, such as a viral delivery vector. To illustrate, the nucleic acid of the invention can be packaged in an AAV particle, an adenovirus particle, a herpesvirus particle, a baculovirus particle, or any other suitable virus particle.

Moreover, the nucleic acid can be operably associated with a promoter element. Promoter elements are described in more detail herein.

The present invention further provides methods of producing the virus vectors of the invention. In a representative embodiment, the present invention provides a method of producing a recombinant virus vector, the method comprising providing to a cell in vitro, (a) a template comprising (i) a heterologous nucleic acid, and (ii) packaging signal sequences sufficient for the encapsidation of the AAV template into virus particles (e.g., one or more (e.g., two) terminal repeats, such as AAV terminal repeats), and (b) AAV sequences sufficient for replication and encapsidation of the template into viral particles (e.g., the AAV rep and AAV cap sequences encoding an AAV capsid of the invention). The template and AAV replication and capsid sequences are provided under conditions such that recombinant virus particles comprising the template packaged within the capsid are produced in the cell. The method can further comprise the step of collecting the virus particles from the cell. Virus particles may be collected from the medium and/or by lysing the cells.

In one illustrative embodiment, the invention provides a method of producing a rAAV particle comprising an AAV capsid, the method comprising: providing a cell in vitro with a nucleic acid encoding a chimeric AAV capsid of the invention, an AAV rep coding sequence, an AAV vector genome comprising a heterologous nucleic acid, and helper functions for generating a productive AAV infection; and allowing assembly of the AAV particles comprising the AAV capsid and encapsidating the AAV vector genome.

The cell is typically a cell that is permissive for AAV viral replication. Any suitable cell known in the art may be employed, such as mammalian cells. Also suitable are trans-complementing packaging cell lines that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so.

The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an EBV based nuclear episome.

As a further alternative, the rep/cap sequences may be stably carried (episomal or integrated) within a cell.

Typically, the AAV rep/cap sequences will not be flanked by the AAV packaging sequences (e.g., AAV ITRs), to prevent rescue and/or packaging of these sequences.

The template (e.g., an rAAV vector genome) can be provided to the cell using any method known in the art. For example, the template may be supplied by a non-viral (e.g., plasmid) or viral vector. In particular embodiments, the template is supplied by a herpesvirus or adenovirus vector (e.g., inserted into the E1a or E3 regions of a deleted adenovirus). As another illustration, Palombo et al., (1998) *J. Virol.* 72:5025, describe a baculovirus vector carrying a reporter gene flanked by the AAV ITRs. EBV vectors may also be employed to deliver the template, as described above with respect to the rep/cap genes.

In another representative embodiment, the template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection are generally provided to the cell. Helper virus sequences necessary for AAV replication are known in the art. Typically, these sequences are provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes integrated in the chromosome or maintained as a stable extrachromosomal element. In representative embodiments, the helper virus sequences cannot be packaged into AAV virions, e.g., are not flanked by AAV ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is optionally a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further contains the rAAV template. The AAV rep/cap sequences and/or the rAAV template may be inserted into a deleted region (e.g., the E1a or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as a "EBV based nuclear episome," see Margolski, (1992) *Curr. Top. Microbiol. Immun.* 158:67).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, in representative embodiments, the adenovirus helper sequences and the AAV rep/cap sequences are not flanked by the AAV packaging sequences (e.g., the AAV ITRs), so that these sequences are not packaged into the AAV virions.

Herpesvirus may also be used as a helper virus in AAV packaging methods. Hybrid herpesviruses encoding the AAV rep protein(s) may advantageously facilitate for more scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described by Urabe et al., (2002) *Human Gene Therapy* 13:1935-43.

Other methods of producing AAV use stably transformed packaging cells (see, e.g., U.S. Pat. No. 5,658,785).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al., (1999) Gene Therapy 6:973). In representative embodiments, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of virus particles. In particular embodiments, the virus stock has a titer of at least about $10^5$ transducing units (tu)/ml, at least about $10^6$ tu/ml, at least about $10^7$ tu/ml, at least about $10^8$ tu/ml, at least about $10^9$ tu/ml, or at least about $10^{10}$ tu/ml.

The novel capsid protein and capsid structures find use in raising antibodies, for example, for diagnostic or therapeutic uses or as a research reagent. Thus, the invention also provides antibodies against the novel capsid proteins and capsids of the invention.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep or human, or can be a chimeric antibody. See, e.g., Walker et al., *Mol. Immunol.* 26, 403-11 (1989). The antibodies can be recombinant monoclonal antibodies, for example, produced according to the methods disclosed in U.S. Pat. No. 4,474,893 or U.S. Pat. No. 4,816,567. The antibodies can also be chemically constructed, for example, according to the method disclosed in U.S. Pat. No. 4,676,980.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254, 1275-1281).

Polyclonal antibodies can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies can be produced in a hybridoma cell line according to the technique of Kohler and Milstein, (1975) *Nature* 265, 495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., W. Huse, (1989) *Science* 246, 1275-81.

Antibodies specific to a target polypeptide can also be obtained by phage display techniques known in the art.

Various immunoassays can be used for screening to identify antibodies having the desired specificity. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes can be used as well as a competitive binding assay.

Antibodies can be conjugated to a solid support (e.g., beads, plates, slides or wells formed from materials such as latex or polystyrene) in accordance with known techniques. Antibodies can likewise be directly or indirectly conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

III. Methods of Using Chimeric AAV Capsids.

The present invention also relates to methods for delivering heterologous nucleotide sequences into oligodendrocytes. The virus vectors of the invention may be employed, e.g., to deliver a nucleotide sequence of interest to an oligodendrocyte in vitro, e.g., to produce a polypeptide or nucleic acid in vitro or for ex vivo gene therapy. The vectors are additionally useful in a method of delivering a nucleotide sequence to a subject in need thereof, e.g., to express a therapeutic or immunogenic polypeptide or nucleic acid. In this manner, the polypeptide or nucleic acid may thus be produced in vivo in the subject. The subject may be in need of the polypeptide or nucleic acid because the subject has a deficiency of the polypeptide, or because the production of the polypeptide or nucleic acid in the subject may impart some therapeutic effect, as a method of treatment or otherwise, and as explained further below.

In particular embodiments, the vectors are useful to express a polypeptide or nucleic acid that provides a beneficial effect to oligodendrocytes, e.g., to promote growth and/or differentiation of oligodendrocytes. The ability to target vectors to oligodendrocytes may be particularly useful to treat diseases or disorders involving oligodendrocyte dysfunction and/or demyelination of neurons. In other embodiments, the vectors are useful to express a polypeptide or nucleic acid that provides a beneficial effect to cells near the oligodendrocytes (e.g., neurons).

Thus, one aspect of the invention relates to a method of delivering a nucleic acid of interest to an oligodendrocyte, the method comprising contacting the oligodendrocyte with the AAV particle of the invention.

In another aspect, the invention relates to a method of delivering a nucleic acid of interest to an oligodendrocyte in a mammalian subject, the method comprising administering an effective amount of the AAV particle or pharmaceutical formulation of the invention to a mammalian subject.

A further aspect of the invention relates to a method of treating a disorder associated with oligodendrocyte dysfunction in a subject in need thereof, the method comprising administering a therapeutically effective amount of the AAV particle of the invention to the subject. In one embodiment, the disorder associated with oligodendrocyte dysfunction is a demyelinating disease. In one embodiment, the disorder associated with oligodendrocyte dysfunction is multiple sclerosis, Pelizaeus-Merzbacher disease, Krabbe's disease, metachromatic leukodystrophy, adrenoleukodystrophy, Canavan disease, Alexander disease, orthochromatic leukodystrophy, Zellweger disease, 18q-syndrome, cerebral palsy, spinal cord injury, traumatic brain injury, stroke, phenylketonuria, or viral infection, or any other disorder known or later found to be associated with oligodendrocyte dysfunction. In another embodiment, the methods of the invention are used to treat a disorder that is not directly associated with oligodendrocyte dysfunction but would benefit by expression of a heterologous polypeptide or nucleic acid in oligodendrocytes in addition to or instead of expression in neurons, astrocytes, or other CNS cell types. Examples include, without limitation, neurodegenerative disorders such as Alzheimer's disease, Parkinson's disease, and Huntington's disease, CNS tumors, and other CNS disorders.

CNS disorders include but are not limited to disorders of thinking and cognition such as schizophrenia and delirium; amnestic disorders; disorders of mood, such as affective disorders and anxiety disorders (including post-traumatic stress disorder, separation anxiety disorder, selective mutism, reactive attachment disorder, stereotypic movement disorder, panic disorders, agoraphobia, specific phobias, social phobia, obsessive-compulsive disorder, acute stress disorder, generalized anxiety disorder, substance-induced anxiety disorder and/or anxiety disorder not otherwise specified); disorders of social behavior; disorders of learning and memory, such as learning disorders (e.g., dyslexia); motor skills disorders; communication disorders (e.g., stuttering); pervasive developmental disorders (e.g., autistic disorder, Rett's disorder, childhood disintegrative disorder, Asperger's disorder, and/or pervasive developmental disorder not otherwise specified) and dementia. Accordingly, the term "central nervous system disorder" encompasses the disorders listed above as well as depressive disorders (including major depressive disorder, dysthmyic disorder, depressive disorder not otherwise specified, postpartum depression); seasonal affective disorder; mania; bipolar disorders (including bipolar I disorder, bipolar II disorder, cyclothymic disorder, bipolar disorder not otherwise specified); attention-deficit and disruptive behavior disorders (including attention deficit disorder with hyperactivity disorder, conduct disorder, oppositional defiant disorder and/or disruptive behavior disorder not otherwise specified); drug addiction/substance abuse (including abuse of opiates, amphetamines, alcohol, hallucinogens, cannabis, inhalants, phencyclidine, sedatives, hypnotics, anxyolytics and/or cocaine); alcohol-induced disorders; amphetamine-induced disorders; caffeine-induced disorders; cannabis-induced disorders; cocaine-induced disorders; hallucinogen-induced disorders; inhalant-induced disorders; nicotine-induced disorders; opioid-induced disorders; phencyclidine-induced disorders; sedative, hypnotic or anxyolytic-induced disorders; agitation; apathy; psychoses; irritability; disinhibition; schizophreniform disorder; schizoaffective disorder; delusional disorder; brief psychotic disorder, shared psychotic disorder; substance-induced psychotic disorder; psychotic disorder not otherwise specified; unipolar disorders, mood disorders (e.g., mood disorder with psychotic features); somatoform disorders; factitious disorders; disassociative disorders; mental retardation; feeding and eating disorders of infancy or early childhood; eating disorders such as anorexia nervosa, bulimia nervosa and/or eating disorder not otherwise specified; sleeping disorders (e.g., dyssomnias such as primary insomnia, primary hypersomnia, narcolepsy, breathing-related sleep disorder and circadian rhythm sleep disorder and/or parasomnias); impulse control disorders (e.g., kleptomania, pyromania, trichotillomania, pathological gambling and/or intermittent explosive disorder); adjustment disorders; personality disorders (e.g., paranoid personality disorder, schizoid personality disorder, schizotypal personality disorder, antisocial personality disorder, borderline personality disorder, histrionic personality disorder, narcissistic personality disorder, avoidant personality disorder, dependent personality disorder and/or obsessive-compulsive personality disorder); Tic disorders (e.g., Tourette's disorder, chronic motor or vocal tic disorder, transient tic disorder and/or tic disorder not otherwise specified); elimination disorders; and any combination of the foregoing as well as any other disorder or group of disorders described in the Diagnostic and Statistical Manual of Mental Disorders—Fourth Edition (DSM-IV; the American Psychiatric Association, Washington D.C., 1994). "Central Nervous System disorders" also include other conditions that implicate the CNS including but not limited to neurodegenerative disorders such as Alzheimer's disease, involuntary movement disorders such as Parkinson's disease, Huntington's disease, amyotrophic lateral sclerosis (ALS), and the like. Other CNS disorders include without limitation epilepsy, multiple sclerosis, neurogenic pain, psychogenic pain, and migraines. In other embodiments, the CNS disorder encompasses any subset of the foregoing diseases or excludes any one or more of the foregoing conditions. In particular embodiments, the term "central nervous system disorder" does not encompass benign and/or malignant tumors of the CNS.

In another aspect of the invention, the chimeric AAV capsid and vectors of the invention are fully- or nearly fully-detargeted vectors that can be further modified to a desirable tropic profile for targeting of one or more peripheral organs or tissues as discussed below. In this aspect, the present invention also relates to methods for delivering heterologous nucleotide sequences into a broad range of cells, including dividing and non-dividing cells. The virus vectors of the invention may be employed to deliver a nucleotide sequence of interest to a cell in vitro, e.g., to produce a polypeptide in vitro or for ex vivo gene therapy. The vectors are additionally useful in a method of delivering a nucleotide sequence to a subject in need thereof, e.g., to express a therapeutic or immunogenic polypeptide or nucleic acid. In this manner, the polypeptide or nucleic acid may thus be produced in vivo in the subject. The subject may be in need of the polypeptide or nucleic acid because the subject has a deficiency of the polypeptide, or because the production of the polypeptide or nucleic acid in the subject may impart some therapeutic effect, as a method of treatment or otherwise, and as explained further below.

In general, the virus vectors of the invention may be employed to deliver any foreign nucleic acid with a biological effect to treat or ameliorate the symptoms associated with any disorder related to gene expression. Further, the invention can be used to treat any disease state for which it is beneficial to deliver a therapeutic polypeptide. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (inhibitory RNA including without limitation RNAi such as siRNA or shRNA, antisense RNA or microRNA to remove repeats), amyotrophic lateral sclerosis, epilepsy (galanin, neurotrophic factors), and other neurological disorders, cancer (endostatin, angiostatin, TRAIL, FAS-ligand, cytokines including interferons; inhibitory RNA including without limitation RNAi (such as siRNA or shRNA), antisense RNA and microRNA including inhibitory RNA against VEGF, the multiple drug resistance gene product or a cancer immunogen), diabetes mellitus (insulin, PGC-α1, GLP-1, myostatin pro-peptide, glucose transporter 4), muscular dystrophies including Duchenne and Becker (e.g., dystrophin, mini-dystrophin, micro-dystrophin, insulin-like growth factor I, a sarcoglycan [e.g., α, β, γ], Inhibitory RNA [e.g., RNAi, antisense RNA or microRNA] against myostatin or myostatin propeptide, laminin-alpha2, Fukutin-related protein, dominant negative myostatin, follistatin, activin type II soluble receptor, anti-inflammatory polypeptides such as the Ikappa B dominant mutant, sarcospan, utrophin, mini-utrophin, inhibitory RNA [e.g., RNAi, antisense RNA or microRNA] against splice junctions in the dystrophin gene to induce exon skipping [see, e.g., WO/2003/095647], inhibitory RNA (e.g., RNAi, antisense RNA or micro RNA] against U7 snRNAs to induce exon skipping [see, e.g., WO/2006/021724], and antibodies or antibody fragments against myostatin or myostatin propeptide), Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects including other lysosomal storage disorders and glycogen storage disorders, congenital emphysema (α1-antitrypsin), Lesch-Nyhan Syndrome (hypoxanthine guanine phosphoribosyl transferase), Niemann-Pick disease (sphingomyelinase), Maple Syrup Urine Disease (branched-chain keto acid dehydrogenase), retinal degenerative diseases (and other diseases of the eye and retina; e.g., PDGF, endostatin and/or angiostatin for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver (RNAi such as siRNA or shRNA, microRNA or antisense RNA for hepatitis B and/or hepatitis C genes), kidney, heart including congestive heart failure or peripheral artery disease (PAD) (e.g., by delivering protein phosphatase inhibitor I [I-1], phospholamban, sarcoplasmic endoreticulum $Ca^{2+}$-ATPase [serca2a], zinc finger proteins that regulate the phospholamban gene, Pim-1, PGC-1α, SOD-1, SOD-2, ECF-SOD, kallikrein, thymosin-β4, hypoxia-inducible transcription factor [HIF], βarket, β2-adrenergic receptor, β2-adrenergic receptor kinase [βARK], phosphoinositide-3 kinase [PI3 kinase], calsarcin, an angiogenic factor, S100A1, parvalbumin, adenylyl cyclase type 6, a molecule that effects G-protein coupled receptor kinase type 2 knockdown such as a truncated constitutively active bARKct, an inhibitory RNA [e.g., RNAi, antisense RNA or microRNA] against phospholamban; phospholamban inhibitory or dominant-negative molecules such as phospholamban S16E, etc.), arthritis (insulin-like growth factors), joint disorders (insulin-like growth factors), intimal hyperplasia (e.g., by delivering enos, inos), improve survival of heart transplants (superoxide dismutase), AIDS (soluble CD4), muscle wasting (insulin-like growth factor I, myostatin pro-peptide, an anti-apoptotic factor, follistatin), limb ischemia (VEGF, FGF, PGC-1α, EC-SOD, HIF), kidney deficiency (erythropoietin), anemia (erythropoietin), arthritis (anti-inflammatory factors such as TRAP and TNFα soluble receptor), hepatitis (α-interferon), LDL receptor deficiency (LDL receptor), hyperammonemia (ornithine transcarbamylase), spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including RANKL and/or VEGF) can be administered with a bone allograft, for example, following a break or surgical removal in a cancer patient.

Exemplary lysosomal storage diseases that can be treated according to the present invention include without limitation: Hurler's Syndrome (MPS IH), Scheie's Syndrome (MPS IS), and Hurler-Scheie Syndrome (MPS IH/S) (α-L-iduronidase); Hunter's Syndrome (MPS II) (iduronate sulfate sulfatase); Sanfilippo A Syndrome (MPS IIIA) (Heparan-S-sulfate sulfaminidase), Sanfilippo B Syndrome (MPS IIIB) (N-acetyl-D-glucosaminidase), Sanfilippo C Syndrome (MPS IIIC) (Acetyl-CoA-glucosaminide N-acetyl-transferase), Sanfilippo D Syndrome (MPS IIID) (N-acetyl-glucosaminine-6-sulfate sulfatase); Morquio A disease (MPS IVA) (Galactosamine-6-sulfate sulfatase), Morquio B disease (MPS IV B) (β-Galactosidase); Maroteaux-lmay disease (MPS VI) (arylsulfatase B); Sly Syndrome (MPS VII) (β-glucuronidase); hyaluronidase deficiency (MPS IX) (hyaluronidase); sialidosis (mucolipidosis I), mucolipidosis II (I-Cell disease) (N-actylglucos-aminyl-1-phosphotransferase catalytic subunit), mucolipidosis III (pseudo-Hurler polydystrophy) (N-acetylglucos-aminyl-1-phosphotransferase; type IIIA [catalytic subunit] and type IIIC [substrate recognition subunit]); GM1 gangliosidosis (ganglioside β-galactosidase), GM2 gangliosidosis Type I (Tay-Sachs disease) (β-hexaminidase A), GM2 gangliosidosis type II (Sandhoff s disease) (β-hexosaminidase B); Niemann-Pick disease (Types A and B) (sphingomyelinase); Gaucher's disease (glucocerebrosidase); Farber's disease (ceraminidase); Fabry's disease (α-galactosidase A); Krabbe's disease (galactosylceramide β-galactosidase); metachromatic leukodystrophy (arylsulfatase A); lysosomal acid lipase deficiency including Wolman's disease (lysosomal acid lipase); Batten disease (juvenile neuronal ceroid lipofuscinosis) (lysosomal trans-membrane CLN3 protein) sialidosis (neuraminidase 1); galactosialidosis (Goldberg's syndrome) (protective protein/cathepsin A); α-mannosidosis (α-D-mannosidase); β-mannosidosis (β-D-mannosidosis); fucosidosis (α-D-fucosidase); aspartylglucosaminuria (N-Aspartylglucosaminidase); and sialuria (Na phosphate cotransporter).

Exemplary glycogen storage diseases that can be treated according to the present invention include, but are not limited to, Type Ia GSD (von Gierke disease) (glucose-6-phosphatase), Type Ib GSD (glucose-6-phosphate translocase), Type Ic GSD (microsomal phosphate or pyrophosphate transporter), Type Id GSD (microsomal glucose transporter), Type II GSD including Pompe disease or infantile Type IIa GSD (lysosomal acid α-glucosidase) and Type IIb (Danon) (lysosomal membrane protein-2), Type IIIa and IIIb GSD (Debrancher enzyme; amyloglucosidase and oligoglucanotransferase), Type IV GSD (Andersen's disease) (branching enzyme), Type V GSD (McArdle disease) (muscle phosphorylase), Type VI GSD (Hers' disease) (liver phosphorylase), Type VII GSD (Tarui's disease) (phosphofructokinase), GSD Type VIII/IXa (X-linked phosphorylase kinase), GSD Type IXb (Liver and muscle phosphorylase kinase), GSD Type IXc (liver phosphorylase kinase), GSD Type IXd (muscle phosphorylase kinase), GSD O (glycogen synthase), Fanconi-Bickel syndrome (glucose transporter-2), phosphoglucoisomerase deficiency, muscle phosphoglycerate kinase deficiency, phosphoglycerate mutase deficiency, fructose 1,6-diphosphatase deficiency, phosphoenolpyruvate carboxykinase deficiency, and lactate dehydrogenase deficiency.

Nucleic acids and polypeptides that can be delivered to cardiac muscle include those that are beneficial in the treatment of damaged, degenerated or atrophied cardiac muscle and/or congenital cardiac defects. For example, angiogenic factors useful for facilitating vascularization in the treatment of heart disease include but are not limited to vascular endothelial growth factor (VEGF), VEGF II, VEGF-B, VEGF-C, VEGF-D, VEGF-E, $VEGF_{121}$, $VEGF_{138}$, $VEGF_{145}$, $VEGF_{165}$, $VEGF_{189}$, $VEGF_{206}$, hypoxia inducible factor lα(HIF 1α), endothelial NO synthase (eNOS), iNOS, VEFGR-1 (Flt1), VEGFR-2 (KDR/Flk1), VEGFR-3 (Flt4), angiogenin, epidermal growth factor (EGF), angiopoietin, platelet-derived growth factor, angiogenic factor, transforming growth factor-α (TGF-α), transforming growth factor-β (TGF-β), vascular permeability factor (VPF), tumor necrosis factor alpha (TNF-α), interleukin-3 (IL-3), interleukin-8 (IL-8), platelet-derived endothelial growth factor (PD-EGF), granulocyte colony stimulating factor (G-CSF), hepatocyte growth factor (HGF), scatter factor (SF), pleitrophin, proliferin, follistatin, placental growth factor (PlGF), midkine, platelet-derived growth factor-BB (PDGF), fractalkine, ICAM-1, angiopoietin-1 and -2 (Ang1 and Ang2), Tie-2, neuropilin-1, ICAM-1, chemokines and cytokines that stimulate smooth muscle cell, monocyte, or leukocyte migration, anti-apoptotic peptides and proteins, fibroblast growth factors (FGF), FGF-1, FGF-1b, FGF-1c, FGF-2, FGF-2b, FGF-2c, FGF-3, FGF-3b, FGF-3c, FGF-4, FGF-5, FGF-7, FGF-9, acidic FGF, basic FGF, monocyte chemotactic protein-1, granulocyte macrophage-colony stimulating factor, insulin-like growth factor-1 (IGF-1), IGF-2, early growth response factor-1 (EGR-1), ETS-1, human tissue kallikrein (HK), matrix metalloproteinase, chymase, urokinase-type plasminogen activator and heparinase. (see, e.g., U.S. Patent Application No. 20060287259 and U.S. Patent Application No. 20070059288).

The most common congenital heart disease found in adults is bicuspid aortic valve, whereas atrial septal defect is responsible for 30-40% of congenital heart disease seen in adults. The most common congenital cardiac defect observed in the pediatric population is ventricular septal defect. Other congenital heart diseases include Eisenmenger's syndrome, patent ductus arteriosus, pulmonary stenosis, coarctation of the aorta, transposition of the great arteries, tricuspid atresia, univentricular heart, Ebstein's anomaly, and double-outlet right ventricle. A number of studies have identified putative genetic loci associated with one or more of these congenital heart diseases. For example, the putative gene(s) for congenital heart disease associated with Down syndrome is 21q22.2-q22.3, between ETS2 and MX1. Similarly, most cases of DiGeorge syndrome result from a deletion of chromosome 22q11.2 (the DiGeorge syndrome chromosome region, or DGCR). Several genes are lost in this deletion including the putative transcription factor TUPLE1. This deletion is associated with a variety of phenotypes, e.g., Shprintzen syndrome; conotruncal anomaly face (or Takao syndrome); and isolated outflow tract defects of the heart including Tetralogy of Fallot, truncus arteriosus, and interrupted aortic arch. All of the foregoing disorders can be treated according to the present invention.

Other significant diseases of the heart and vascular system are also believed to have a genetic, typically polygenic, etiological component. These diseases include, for example, hypoplastic left heart syndrome, cardiac valvular dysplasia, Pfeiffer cardiocranial syndrome, oculofaciocardiodental syndrome, Kapur-Toriello syndrome, Sonoda syndrome, Ohdo Blepharophimosis syndrome, heart-hand syndrome, Pierre-Robin syndrome, Hirschsprung disease, Kousseff syndrome, Grange occlusive arterial syndrome, Kearns-Sayre syndrome, Kartagener syndrome, Alagille syndrome, Ritscher-Schinzel syndrome, Ivemark syndrome, Young-Simpson syndrome, hemochromatosis, Holzgreve syndrome, Barth syndrome, Smith-Lemli-Opitz syndrome, glycogen storage disease, Gaucher-like disease, Fabry disease, Lowry-Maclean syndrome, Rett syndrome, Opitz syndrome, Marfan syndrome, Miller-Dieker lissencephaly syndrome, mucopolysaccharidosis, Bruada syndrome, humerospinal dysostosis, Phaver syndrome, McDonough syndrome, Marfanoid hypermobility syndrome, atransferrinemia, Cornelia de Lange syndrome, Leopard syndrome, Diamond-Blackfan anemia, Steinfeld syndrome, progeria, and Williams-Beuren syndrome. All of these disorders can be treated according to the present invention.

Anti-apoptotic factors can be delivered to skeletal muscle, diaphragm muscle and/or cardiac muscle to treat muscle wasting diseases, limb ischemia, cardiac infarction, heart failure, coronary artery disease and/or type I or type II diabetes.

Nucleic acids that can be delivered to skeletal muscle include those that are beneficial in the treatment of damaged, degenerated and/or atrophied skeletal muscle. The genetic defects that cause muscular dystrophy are known for many forms of the disease. These defective genes either fail to produce a protein product, produce a protein product that fails to function properly, or produce a dysfunctional protein product that interferes with the proper function of the cell. The heterologous nucleic acid may encode a therapeutically functional protein or a polynucleotide that inhibits production or activity of a dysfunctional protein. Polypeptides that may be expressed from delivered nucleic acids, or inhibited by delivered nucleic acids (e.g., by delivering RNAi, microRNA or antisense RNA), include without limitation dystrophin, a mini-dystrophin or a micro-dystrophin (Duchene's and Becker MD); dystrophin-associated glycoproteins β-sarcoglycan (limb-girdle MD 2E), δ-sarcoglycan (limb-girdle MD 2 2F), α-sarcoglycan (limb girdle MD 2D) and γ-sarcoglycan (limb-girdle MD 2C), utrophin, calpain (autosomal recessive limb-girdle MD type 2A), caveolin-3 (autosomal-dominant limb-girdle MD), laminin-alpha2 (merosin-deficient congenital MD), miniagrin (laminin-alpha2 deficient congenital MD), fukutin (Fukuyama type congenital MD), emerin (Emery-Dreifuss MD), myotilin, lamin A/C, calpain-3, dysferlin, and/or telethonin. Further, the heterologous nucleic acid can encode mir-1, mir-133, mir-206, mir-208 or an antisense RNA, RNAi (e.g., siRNA or shRNA) or microRNA to induce exon skipping in a defective dystrophin gene.

In particular embodiments, the nucleic acid is delivered to tongue muscle (e.g., to treat dystrophic tongue). Methods of delivering to the tongue can be by any method known in the art including direct injection, oral administration, topical administration to the tongue, intravenous administration, intra-articular administration and the like.

The foregoing proteins can also be administered to diaphragm muscle to treat muscular dystrophy.

Alternatively, a gene transfer vector may be administered that encodes any other therapeutic polypeptide.

In particular embodiments, a virus vector according to the present invention is used to deliver a nucleic acid of interest as described herein to skeletal muscle, diaphragm muscle and/or cardiac muscle, for example, to treat a disorder associated with one or more of these tissues such as muscular dystrophy, heart disease (including PAD and congestive heart failure), and the like.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using inhibitory RNA such as RNAi (e.g., siRNA or shRNA), microRNA or antisense RNA. For unbalanced disease states, gene transfer can be used to create a disease state in a model system, which can then be used in efforts to counteract the disease state. Thus, the virus vectors according to the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The virus vectors according to the present invention may also be employed to provide an antisense nucleic acid or inhibitory RNA (e.g., microRNA or RNAi such as a siRNA or shRNA) to a cell in vitro or in vivo. Expression of the inhibitory RNA in the target cell diminishes expression of a particular protein(s) by the cell. Accordingly, inhibitory RNA may be administered to decrease expression of a particular protein in a subject in need thereof. Inhibitory RNA may also be administered to cells in vitro to regulate cell physiology, e.g., to optimize cell or tissue culture systems.

As a further aspect, the virus vectors of the present invention may be used to produce an immune response in a subject. According to this embodiment, a virus vector comprising a nucleic acid encoding an immunogen may be administered to a subject, and an active immune response (optionally, a protective immune response) is mounted by the subject against the immunogen. Immunogens are as described hereinabove.

Alternatively, the virus vector may be administered to a cell ex vivo and the altered cell is administered to the subject. The heterologous nucleic acid is introduced into the cell, and the cell is administered to the subject, where the heterologous nucleic acid encoding the immunogen is optionally expressed and induces an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

The virus vectors of the present invention may also be administered for cancer immunotherapy by administration of a viral vector expressing a cancer cell antigen (or an immunologically similar molecule) or any other immunogen that produces an immune response against a cancer cell. To illustrate, an immune response may be produced against a cancer cell antigen in a subject by administering a viral vector comprising a heterologous nucleotide sequence encoding the cancer cell antigen, for example to treat a patient with cancer. The virus vector may be administered to a subject in vivo or by using ex vivo methods, as described herein.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to, leukemia, lymphoma (e.g., Hodgkin and non-Hodgkin lymphomas), colorectal cancer, renal cancer, liver cancer, breast cancer, lung cancer, prostate cancer, testicular cancer, ovarian cancer, uterine cancer, cervical cancer, brain cancer (e.g., gliomas and glioblastoma), bone cancer, sarcoma, melanoma, head and neck cancer, esophageal cancer, thyroid cancer, and the like. In embodiments of the invention, the invention is practiced to treat and/or prevent tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

Cancer cell antigens have been described hereinabove. By the terms "treating cancer" or "treatment of cancer," it is intended that the severity of the cancer is reduced or the cancer is prevented or at least partially eliminated. For example, in particular contexts, these terms indicate that metastasis of the cancer is prevented or reduced or at least partially eliminated. In further representative embodiments, these terms indicate that growth of metastatic nodules (e.g., after surgical removal of a primary tumor) is prevented or reduced or at least partially eliminated. By the terms "prevention of cancer" or "preventing cancer" it is intended that the methods at least partially eliminate or reduce the incidence or onset of cancer. Alternatively stated, the onset or progression of cancer in the subject may be slowed, controlled, decreased in likelihood or probability, or delayed.

In particular embodiments, cells may be removed from a subject with cancer and contacted with a virus vector according to the present invention. The modified cell is then administered to the subject, whereby an immune response against the cancer cell antigen is elicited. This method is particularly advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (e.g., CTL inductive cytokines) may be administered to a subject in conjunction with the virus vectors.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

The viral vectors are further useful for targeting oligodendrocytes for research purposes, e.g., for study of CNS function in vitro or in animals or for use in creating and/or studying animal models of disease. For example, the vectors can be used to deliver heterologous nucleic acids to oligodendrocytes in animal models of demyelinating diseases. Demyelination can be induced in animals by a variety of means, including without limitation administration of viruses (e.g., Semliki virus, murine hepatitis virus, or Theiler's murine encephalomyelitis virus) and administration of chemicals (e.g., cuprizone, ethidium bromide, or lysolecithin). In some embodiments, the vector can also be used in animal models of experimental autoimmune encephalomyelitis. This condition can be induced by, for example, administration of kainite, SIN-1, anti-galactocerebroside, or irradiation. In other embodiments, the viral vector can be used to specifically deliver to oligodendrocytes a toxic agent or an enzyme that produces a toxic agent (e.g., thymidine kinase) in order to kill some or all of the cells.

Further, the virus vectors according to the present invention find further use in diagnostic and screening methods, whereby a gene of interest is transiently or stably expressed in a cell culture system, or alternatively, a transgenic animal model. The invention can also be practiced to deliver a nucleic acid for the purposes of protein production, e.g., for laboratory, industrial or commercial purposes.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a nucleic acid including those described herein. For example, in particular embodiments, the subject has (or has had) or is at risk for a demyelinating disorder or a spinal cord or brain injury. As a further option, the subject can be a laboratory animal and/or an animal model of disease.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleotide sequence to a cell in vitro. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the virus vector can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell (cancers and tumors are described above). Moreover, the cells can be from any species of origin, as indicated above.

The virus vectors may be introduced to cells in vitro for the purpose of administering the modified cell to a subject. In particular embodiments, the cells have been removed from a subject, the virus vector is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the recombinant virus vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

In some embodiments, cells that have been transduced with the virus vector may be administered to elicit an immunogenic response against the delivered polypeptide (e.g., expressed as a transgene or in the capsid). Typically, a quantity of cells expressing an effective amount of the polypeptide in combination with a pharmaceutically acceptable carrier is administered. Optionally, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vectors or capsids of the invention to subjects. In particular embodiments, the method comprises a method of delivering a nucleic acid of interest to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

The virus vectors of the invention can further be administered to a subject to elicit an immunogenic response (e.g., as a vaccine). Typically, vaccines of the present invention comprise an effective amount of virus in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^3$, $10^{14}$, $10^{15}$ transducing units or more, preferably about $10^7$ or $10^8$, $10^9$, $10^{10}$, $10^{11}$, $10^{12}$, $10^{13}$ or $10^{14}$ transducing units, yet more preferably about $10^{12}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and on the nature of the particular vector that is being used.

In some embodiments, the viral vector is administered directly to the CNS, e.g., the brain or the spinal cord. Direct administration can result in high specificity of transduction of oligodendrocytes, e.g., wherein at least 80%, 85%, 90%, 95% or more of the transduced cells are oligodendrocytes. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intranasal, intra-aural, intra-ocular (e.g., intravitreous, sub-retinal, anterior chamber) and peri-ocular (e.g., sub-Tenon's region) delivery or any combination thereof.

Typically, the viral vector will be administered in a liquid formulation by direct injection (e.g., stereotactic injection) to the desired region or compartment in the CNS. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. Controlled release of parvovirus and AAV vectors is described by international patent publication WO 01/91803.

In some embodiments where the subject has a compromised blood-brain barrier (BBB), the viral vector can be delivered systemically (e.g., intravenously) to the subject, wherein the vector transduces oligodendrocytes in the area of (e.g., bordering) the BBB compromise. In certain embodiments, the vector transduces cells in the compromised area but not cells in uncompromised areas. Thus, one aspect of the invention relates to a method of delivering a nucleic acid of interest to an area of the CNS bordering a compromised blood brain barrier area in a mammalian subject, the method comprising intravenously administering an effective amount of the AAV particle of the invention.

In some embodiments, the compromise in the BBB is due to a disease or disorder. Examples include, without limitation, neurodegenerative diseases such as Alzheimer's, Parkinson's disease, disease, amyotrophic lateral sclerosis, and multiple sclerosis, epilepsy, CNS tumors, or cerebral infarcts. In other embodiments, the BBB compromise can be an induced disruption, e.g., to promote delivery of agents to the CNS. Temporary BBB compromises can be induced by, for example, toxic chemicals (such as metrazol, VP-16, cisplatin, hydroxyurea, fluorouracil, and etoposide), osmotic agents (such as mannitol and arabinose), biological agents (such as retinoic acid, phorbol myristate acetate, leukotriene C4, bradykinin, histamine, RMP-7, and alkylglycerols), or irradiation (such as ultrasound or electromagnetic radiation).

Administration to skeletal muscle according to the present invention includes but is not limited to administration to skeletal muscles in the limbs (e.g., upper arm, lower arm, upper leg, and/or lower leg), back, neck, head (e.g., tongue), thorax, abdomen, pelvis/perineum, and/or digits. Suitable skeletal muscle tissues include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor and any other suitable skeletal muscle as known in the art.

The virus vector can be delivered to skeletal muscle by any suitable method including without limitation intravenous administration, intra-arterial administration, intraperitoneal administration, isolated limb perfusion (of leg and/or arm; see, e.g. Arruda et al., (2005) *Blood* 105:3458-3464), and/or direct intramuscular injection.

Administration to cardiac muscle includes without limitation administration to the left atrium, right atrium, left ventricle, right ventricle and/or septum. The virus vector can be delivered to cardiac muscle by any method known in the art including, e.g., intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to any of these tissues can also be achieved by delivering a depot comprising the virus vector, which can be implanted into the skeletal, cardiac and/or diaphragm muscle tissue or the tissue can be contacted with a film or other matrix comprising the virus vector. Examples of such implantable matrices or substrates are described in U.S. Pat. No. 7,201,898.

In particular embodiments, a virus vector according to the present invention is administered to skeletal muscle, diaphragm muscle and/or cardiac muscle (e.g., to treat muscular dystrophy or heart disease [for example, PAD or congestive heart failure]).

The invention can be used to treat disorders of skeletal, cardiac and/or diaphragm muscle. Alternatively, the invention can be practiced to deliver a nucleic acid to skeletal, cardiac and/or diaphragm muscle, which is used as a platform for production of a protein product (e.g., an enzyme) or non-translated RNA (e.g., RNAi, microRNA, antisense RNA) that normally circulates in the blood or for systemic delivery to other tissues to treat a disorder (e.g., a metabolic disorder, such as diabetes (e.g., insulin), hemophilia (e.g., Factor IX or Factor VIII), or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating metabolic disorders are described above.

In a representative embodiment, the invention provides a method of treating muscular dystrophy in a subject in need thereof, the method comprising: administering an effective amount of a virus vector of the invention to a mammalian subject, wherein the virus vector comprises a heterologous nucleic acid effective to treat muscular dystrophy. In an exemplary embodiment, the method comprises: administering an effective amount of a virus vector of the invention to a mammalian subject, wherein the virus vector comprises a heterologous nucleic acid encoding dystrophin, a mini-dystrophin, a micro-dystrophin, utrophin, mini-utrophin, laminin-α2, mini-agrin, Fukutin-related protein, follistatin, dominant negative myostatin, α-sarcoglycan, β-sarcoglycan, γ-sarcoglycan, δ-sarcoglycan, IGF-1, myostatin propeptide, activin type II soluble receptor, anti-inflammatory polypeptides such as the Ikappa B dominant mutant, sarcospan, antibodies or antibody fragments against myostatin or myostatin propeptide, or an inhibitory RNA (e.g., antisense RNA, microRNA or RNAi) against myostatin, mir-1, mir-133, mir-206, mir-208 or an inhibitory RNA (e.g., microRNA, RNAi or antisense RNA) to induce exon skipping in a defective dystrophin gene. In particular embodiments, the virus vector can be administered to skeletal, diaphragm and/or cardiac muscle as described elsewhere herein.

The invention further encompasses a method of treating a metabolic disorder in a subject in need thereof. In representative embodiments, the method comprises: administering an effective amount of a virus vector of the invention to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. As a further option, the heterologous nucleic acid can encode a secreted protein. The invention can also be practiced to produce inhibitory RNA (e.g., antisense RNA, microRNA or RNAi) for systemic delivery.

The invention also provides a method of treating congenital heart failure in a subject in need thereof, the method comprising administering an effective amount of a virus vector of the invention to a mammalian subject, wherein the virus vector comprises a heterologous nucleic acid effective to treat congenital heart failure. In representative embodiments, the method comprises administering an effective amount of a virus vector of the invention to a mammalian subject, wherein the virus vector comprises a heterologous nucleic acid encoding a sarcoplasmic endoreticulum $Ca^{2+}$-ATPase (SERCA2a), an angiogenic factor, phospholamban, PI3 kinase, calsarcan, a (β-adrenergic receptor kinase ((βARK), βARKct, inhibitor 1 of protein phosphatase 1, Pim-1, PGC-1α, SOD-1, SOD-2, EC-SOD, Kallikrein, HIF, thymosin-β4, S100A1, parvalbumin, adenylyl cyclase type 6, a molecule that effects G-protein coupled receptor kinase type 2 knockdown such as a truncated constitutively active bARKct; phospholamban inhibitory or dominant-negative molecules such as phospholamban S16E, mir-1, mir-133, mir-206, mir-208.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, and/or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

IV. Use of the AAV Capsid to Target Peripheral Tissues.

Figure 4:
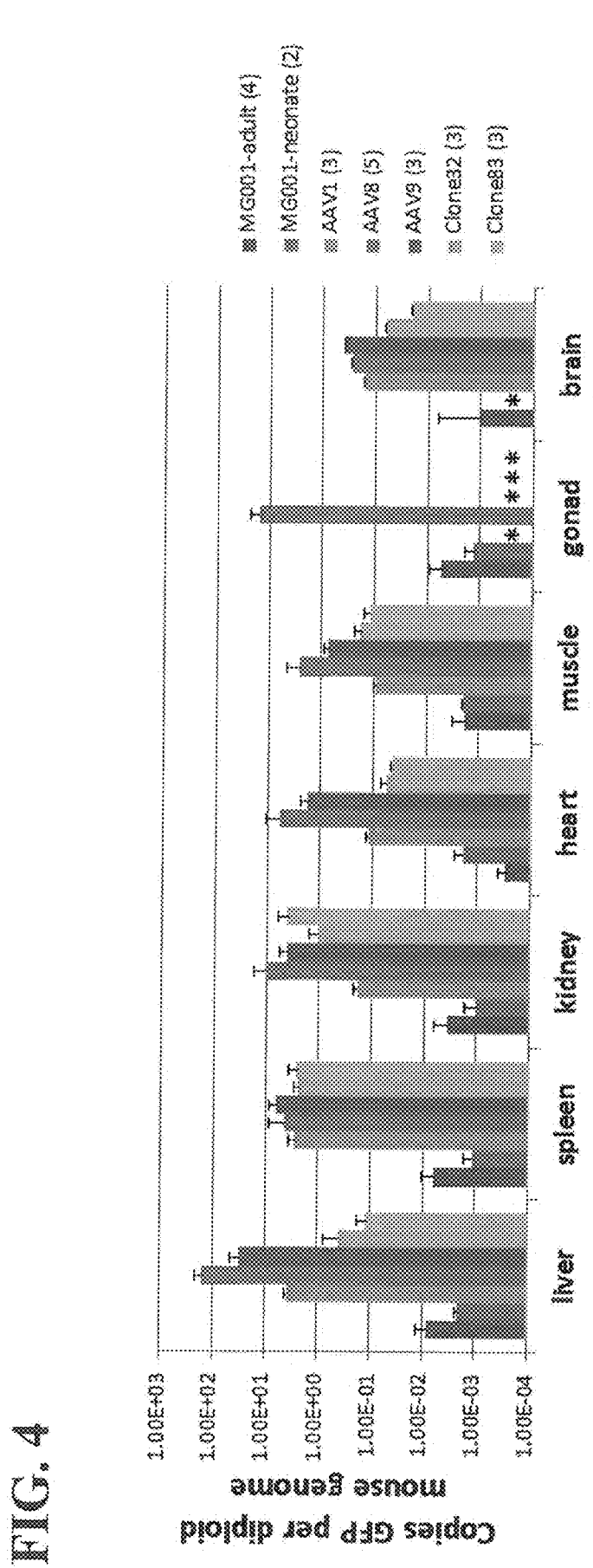
FIG. 4 shows the biodistribution of BNP61 (MG001) and parent capsids after intravenous injection in female wild-type mice, determined by quantitative PCR. The Y-axis is copies of GFP per diploid mouse genome.

The AAV capsids and vectors of the present invention have been demonstrated to be fully or nearly fully detargeted for peripheral organs and tissues (see FIG. 4). This detargeting makes the vectors ideal as a "blank" vector that can be altered to produce the desired tropic profile, e.g., to target specific organs and tissues and/or detarget other organs and tissues. Thus, one aspect of the invention relates to a method of preparing an AAV capsid having a tropism profile of interest, the method comprising modifying the AAV capsid of the present invention to insert an amino acid sequence providing the tropism profile of interest. In some embodiments, the tropism profile of interest is enhanced selectivity for a tissue selected from skeletal muscle, cardiac muscle, diaphragm, kidney, liver, pancreas, spleen, gastrointestinal tract, lung, joint tissue, tongue, ovary, testis, a germ cell, a cancer cell, or a combination thereof and/or reduced selectivity for a tissue selected from liver, ovary, testis, a germ cell, or a combination thereof.

Examples of specific targeting and detargeting sequences are known in the art. One example is the molecular basis for preferential liver tropism, which has been mapped, in the case of AAV2 and AAV6, to a continuous basic footprint that appears to be involved in the interaction of either serotype with heparin. Specifically, it has previously been demonstrated that a single lysine residue on AAV6 (K531) dictates heparin binding ability and consequently, liver tropism. In corollary, substitutional mutagenesis of the corresponding glutamate/aspartate residue on other serotypes with a lysine residue confers heparin binding, possibly by forming a minimum continuous basic footprint on the capsid surface. Another example is the capsid mutants comprising alterations in the three-fold axis loop 4 as disclosed in International Publication No. WO 2012/093784, incorporated herein by reference in its entirety. These mutants exhibit one or more properties including (i) reduced transduction of liver, (ii) enhanced movement across endothelial cells, (iii) systemic transduction; (iv) enhanced transduction of muscle tissue (e.g., skeletal muscle, cardiac muscle and/or diaphragm muscle), and/or (v) reduced transduction of brain tissues (e.g., neurons). Other tropic sequences are described in Li et al., (2012) J. Virol. 86:7752-7759; Pulicherla et al., (2011) Mol. Ther. 19:1070-1078; Bowles et al., (2012) Mol. Ther. 20:443-455; Asokan et al., (2012) Mol. Ther. 20:699-708; and Asokan et al., (2010) Nature Biotechnol. 28:79-82; each incorporated by reference in its entirety.

In some embodiments, the AAV capsid of the present invention can be modified through DNA scrambling and/or directed evolution to identify modified capsids having the desired tropism profile. Techniques for DNA scrambling and directed evolution of AAV capsids are described in International Publication No. WO 2009/137006, incorporated herein by reference in its entirety.

Having described the present invention, the same will be explained in greater detail in the following examples, which are included herein for illustration purposes only, and which are not intended to be limiting to the invention.

EXAMPLE 1

Discovery and Characterization of the BNP61 AAV Clone

A mutant DNA shuffled AAV capsid library was injected intravenously into a rat model of Parkinson's disease and 3 days later cells were dissociated from the caudate nucleus. Using PCR rescue, a single clone emerged (BNP61). Additional shuffling and selection yielded the same clone. As seen in FIG. 1, this clone is a chimera of several AAV serotypes.

Figures 2A, 2B, 2C:
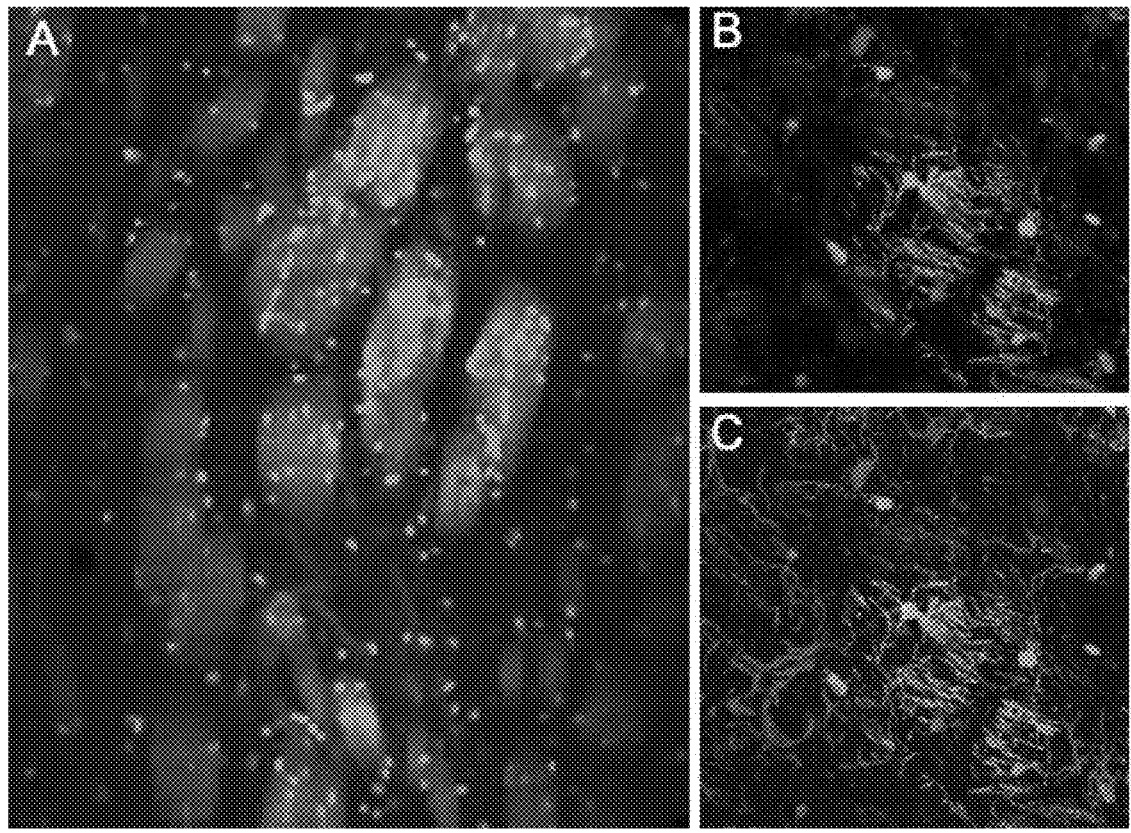
FIGS. 2A-2C show the tropism of BNP61 for oligodendrocytes in rat caudate. (A) shows GFP positive oligodendrocytes in the rat caudate 1 week after the infusion of BNP61-CBh-GFP vectors. Note that there are no GFP positive neurons. (B) shows a higher magnification that reflects clear oligodendrocyte morphology, and (C) shows that none of the GFP positive cells colocalize with the cellular marker for astrocytes, GFAP(red).

Direct infusion of this BNP61 clone into the rat brain produced a surprising cellular transduction pattern. To date, almost all diverse AAV serotypes and chimeras exhibit a >95% tropism for neurons, when gene expression is driven by a constitutive promoter. In marked contrast, BNP61 exhibited a >95% tropism for oligodendrocytes with no evidence of astrocyte or microglial transduction and minimal neuronal transduction (FIGS. 2A-2C). FIG. 2A shows GFP positive oligodendrocytes in the rat caudate 1 week after the infusion of BNP61-CBh-GFP vectors. Note that there are no GFP positive neurons. FIG. 2B shows a higher magnification that reflects clear oligodendrocyte morphology, and FIG. 2C shows that none of the GFP positive cells colocalize with the cellular marker for astrocytes, GFAP (red).

Figures 3A, 3B:
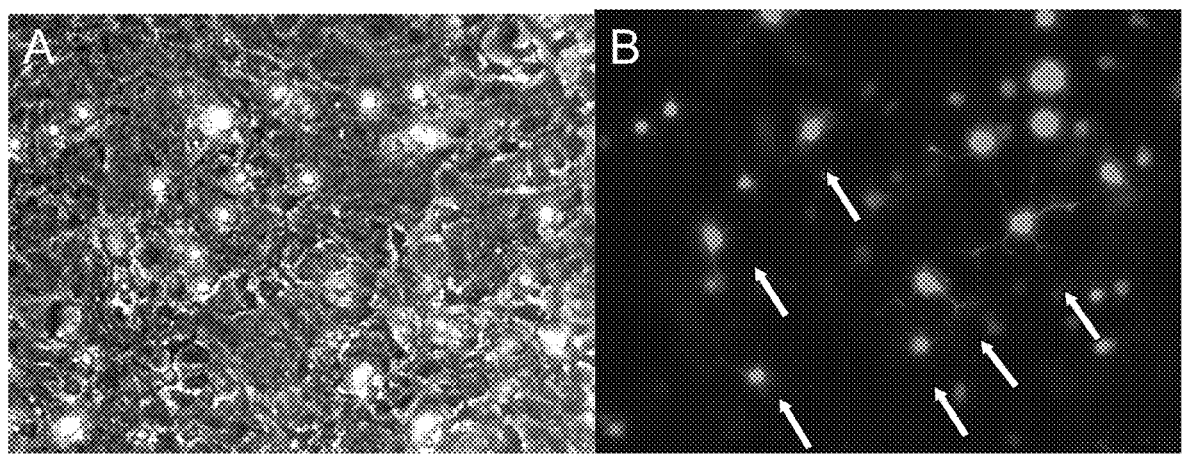
FIGS. 3A-3B show the tropism of BNP61 for oligodendrocytes in primary oligodendrocyte cultures.

Also, in primary oligodendrocyte cultures, BNP61 transduces the oligodendrocytes but not the underlying bed of astrocytes (FIGS. 3A-3B). Mixed glial cultures at day 10 were transduced with BNP61-GFP at a MOI of 100 viral particles and images were taken 72 hr later. FIG. 3A is a light image of the glial culture. FIG. 3B is an image of fluorescent AAV GFP-positive cells taken from the same frame as FIG. 3A. The underlayer bed of astrocytes was not transduced and nearly all GFP-expressing cells appear morphologically as oligodendrocytes. Arrows indicate near-focused oligodendrocytes showing processes consistent with oligodendrocyte progenitor culture morphology. Thus, the BNP61 AAV vector exhibits properties that are distinctly different from other AAV vectors characterized to date.

In order to assess peripheral biodistribution, mice received intravenous administration of BNP61-CBh-GFP vectors and subsequently the peripheral organs were harvested. All mice were injected as adults with $5 \times 10^{10}$ vg except as indicated. Neonatal injections were with $2.5 \times 10^{10}$ vg. Adults were sacrificed 10 days post-injection, and neonates were sacrificed at 4 weeks post-injection. * indicates samples not tested. In the legend, the number of animals for each vector is shown in parentheses. Error bars are S.E.M. As seen in FIG. 4, BNP61 did not accumulate in any of the peripheral organs.

EXAMPLE 2

BNP61 Crosses the Compromised Blood-Brain Barrier

Figure 5:
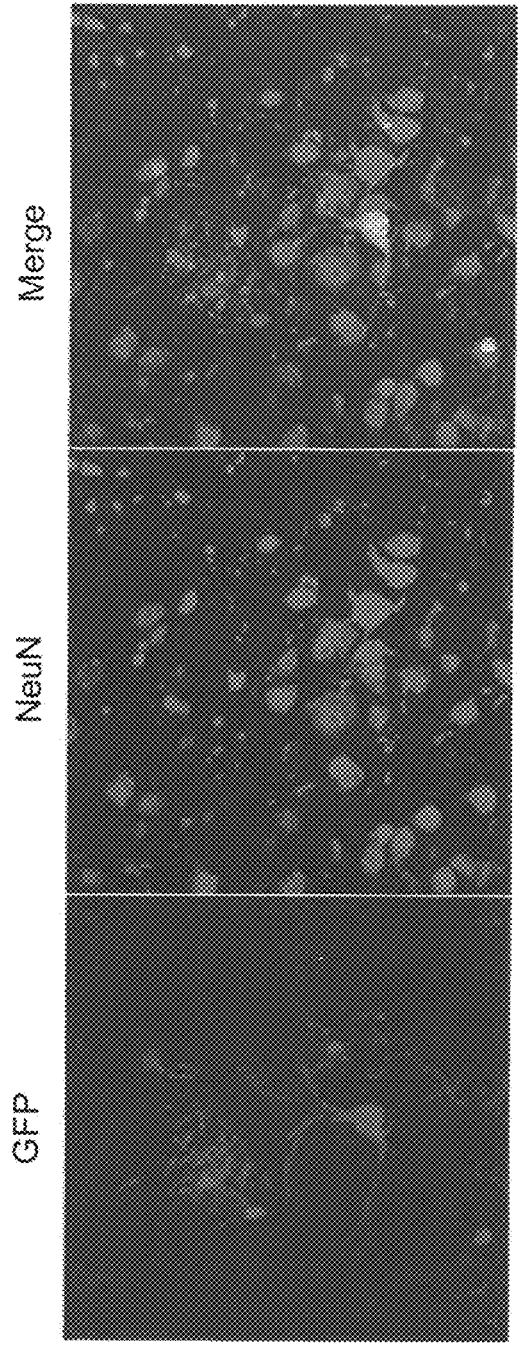
FIG. 5 shows that BNP61 crosses the compromised blood-brain barrier after peripheral administration.

After the first selection round, the BNP61 clone was packaged with GFP and recombinant virus was produced. Then, 2 weeks post-6-OHDA treatment the recombinant virus was administered intravenously at a dose of $8 \times 10^{11}$ vector genomes/kg. One month later, the rats were sacrificed and the brains sectioned. In these 2 week post treatment rats, substantial gene expression was found in oligodendrocytes and some neurons within the 6-OHDA treated striatum (FIG. 5), while no gene expression was found in the contralateral striatum, the injector tract in the cortex or distal brain structures. Note the lack of NeuN co-localization with the many oligodendrocytes that surround the lone NeuN positive neuron (FIG. 5). Thus, it appears that after intravenous administration this novel AAV clone exhibits the ability to cross the 6-OHDA compromised blood-brain barrier, but not the intact blood-brain barrier.

EXAMPLE 3

Generation of Additional Oligodendrocyte Targeted Clones

Using the same AAV DNA capsid shuffling and in vivo directed evolution process described in Example 1, two additional oligodendrocyte-targeted clones were identified, BNP62 and BNP63. As shown in FIG. 1 and similar to BNP61, these clones are chimeras of several AAV serotypes. The amino acid sequence identity between the three clones is shown in Table 2. All three clones are greater than 95% identical to each other at the amino acid level.

TABLE 2

Sequence identity between clones

|  | BNP61 | BNP62 | BNP63 |
|---|---|---|---|
| BNP61 | 100% | 96% | 97% |
| BNP62 | 96% | 100% | 96% |
| BNP63 | 97% | 96% | 100% |

Figure 6:
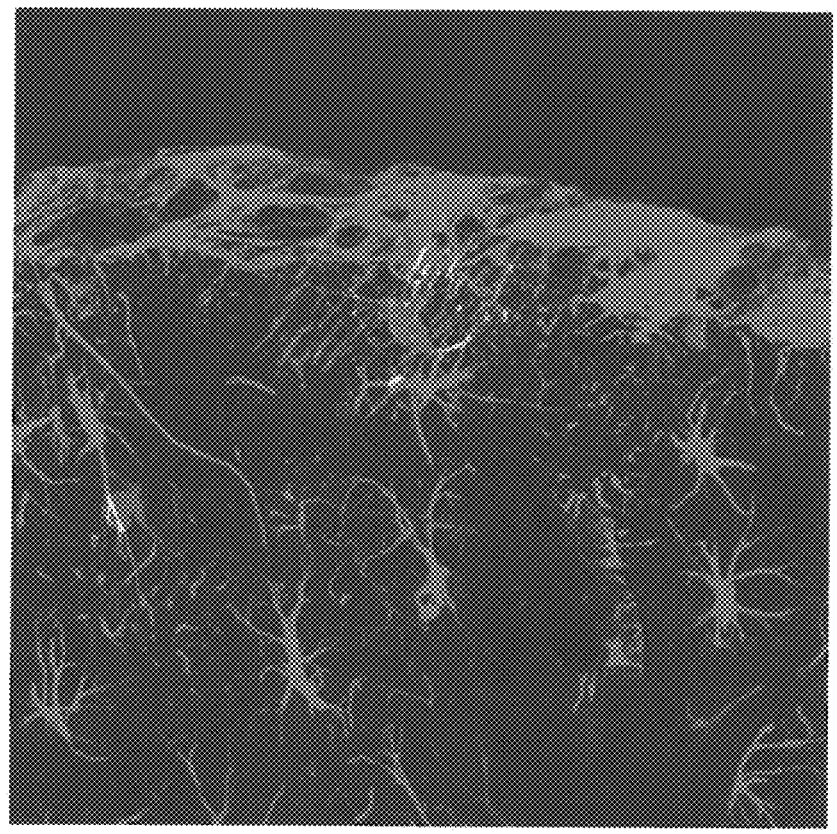
FIG. 6 shows the tropism of BNP63 for oligodendrocytes in rat piriform cortex.

FIG. 6 shows that the BNP63 clone transduces oligodendrocytes in the rat piriform cortex. The BNP63 transduced cells (green) do not co-localize with a cellular marker for astrocytes (GFAP, red). Also, the transduced cells exhibit a clear oligodendrocyte morphology.

The foregoing is illustrative of the present invention, and is not to be construed as limiting thereof. The invention is defined by the following claims, with equivalents of the claims to be included therein.

We claim:

1. A method of delivering a nucleic acid of interest to an oligodendrocyte, the method comprising directly contacting the oligodendrocyte with an adeno-associated virus (AAV) particle comprising:
an AAV vector genome comprising or encoding the nucleic acid of interest encapsidated by—an AAV capsid comprising an amino acid sequence at least 96% identical to SEQ ID NOS: 2 or 4, that exhibits a preferential tropism for oligodendrocytes as compared to astrocytes, microglia and neurons.

2. The method of claim 1, wherein the amino acid sequence is SEQ ID NOS: 2 or 4, wherein 25 or fewer amino acids are substituted, deleted, and/or inserted.

3. The method of claim 2, wherein 25 or fewer amino acids are substituted, and/or 1 amino acid deleted, and/or inserted, wherein the substitutions, deletion and/or insertion do not unduly impair the structure and/or function of an AAV virion comprising the capsid.

4. The method of claim 1, wherein the amino acid sequence is SEQ ID NOS: 2 or 4.

5. The method of claim 4, wherein the amino acid sequence is SEQ ID NO:2.

6. The method of claim 4, wherein the amino acid sequence is SEQ ID NO:4.

7. The method of claim 1, wherein contacting occurs in vitro.

8. The method of claim 1, wherein contacting occurs in vivo.

9. A method of delivering a nucleic acid of interest to an oligodendrocyte in a mammalian subject, the method comprising:
directly administering to the central nervous system (CNS) of the subject to thereby contact oligodendrocytes within the CNS, an effective amount of a pharmaceutical formulation comprising an adeno-associated virus (AAV) particle comprising:
an AAV vector genome comprising or encoding the nucleic acid of interest encapsidated by an AAV capsid comprising an amino acid sequence at least 96% identical to SEQ ID NOS: 2 or 4, that exhibits a preferential tropism for oligodendrocytes as compared to astrocytes, microglia and neurons.

10. The method of claim 9, wherein the mammalian subject is a human subject.

11. The method of claim 9, wherein the AAV particle is delivered directly to the CNS by intrathecal, intracerebral, intraventricular, intranasal, intra-aural, intra-ocular, or peri-ocular administration of the pharmaceutical formulation, or any combination thereof.

12. The method of claim 9, wherein the subject has a disorder associated with oligodendrocyte dysfunction.

13. The method of claim 12, wherein the disorder associated with oligodendrocyte dysfunction is a demyelinating disease.

14. The method of claim 12, wherein the disorder associated with oligodendrocyte dysfunction is multiple sclerosis, Pelizaeus-Merzbacher disease, Krabbe's disease, metachromatic leukodystrophy, adrenoleukodystrophy, Canavan disease, Alexander disease, orthochromatic leukodystrophy, Zellweger disease, 18q-syndrome, cerebral palsy, spinal cord injury, traumatic brain injury, stroke, phenylketonuria, or viral infection.

15. The method of claim 9, wherein the amino acid sequence is SEQ ID NOS: 2 or 4, wherein 25 or fewer amino acids are substituted.

16. The method of claim 15, wherein 25 or fewer amino acids are substituted, and/or 1 amino acid deleted, and/or inserted, wherein the substitutions, deletion and/or insertion do not unduly impair the structure and/or function of an AAV virion comprising the capsid.

17. The method of claim 9, wherein the amino acid sequence is SEQ ID NOS: 2 or 4.

18. The method of claim 9, wherein the amino acid sequence is SEQ ID NOS: 2 or 4, wherein 10 or fewer amino acids are substituted, deleted, and/or inserted.

19. The method of claim 18, wherein the amino acid sequence is SEQ ID NOS: 2 or 4, wherein 10 or fewer amino acids are substituted with a conservative amino acid substitution.

20. A method of delivering a nucleic acid of interest to an area of the CNS bordering a compromised blood-brain barrier area in a mammalian subject, the method comprising:
intravenously administering to the subject with a compromised blood-brain barrier an effective amount of an adeno-associated virus (AAV) particle comprising:
an AAV vector genome comprising or encoding the nucleic acid of interest encapsidated by an AAV capsid comprising an amino acid sequence at least 96% identical to SEQ ID NOS: 2 or 4, that exhibits the ability to cross a compromised blood-brain barrier and a preferential tropism for oligodendrocytes as compared to astrocytes, microglia and neurons.

21. The method of claim 20, wherein the amino acid sequence is SEQ ID NOS: 2 or 4, wherein 25 or fewer amino acids are substituted.

22. The method of claim 21, wherein 25 or fewer amino acids are substituted, and/or 1 amino acid deleted, and/or inserted, wherein the substitutions, deletion and/or insertion do not unduly impair the structure and/or function of an AAV virion comprising the capsid.

23. The method of claim 20, wherein the amino acid sequence is SEQ ID NOS: 2 or 4, wherein 10 or fewer, 5 or fewer, 4 or fewer, 3 or fewer, 2 or fewer, or 1 or fewer amino acids are substituted, deleted, and/or inserted.

* * * * *

UNITED STATES PATENT AND TRADEMARK OFFICE
CERTIFICATE OF CORRECTION

PATENT NO. : 12,076,351 B2
APPLICATION NO. : 16/511913
DATED : September 3, 2024
INVENTOR(S) : McCown et al.

Page 1 of 1

It is certified that error appears in the above-identified patent and that said Letters Patent is hereby corrected as shown below:

In the Specification

Column 5, Line 12: Please insert --TABLE 1-- before the table

Columns 9-10, Line 41: Please correct "Capside" to read --Capsid--

Column 13, Line 9: Please correct "KNIPVPADPP" to read --KNTPVPADPP--

Column 16, Line 66: Please correct "≠2," to read --β,--

Column 33, Line 42: Please correct "TRAP" to read --IRAP--

Column 34, Line 12: Please correct "(Sandhoff s disease)" to read --(Sandhoff's disease)--

Signed and Sealed this
Twenty-sixth Day of November, 2024

Katherine Kelly Vidal
*Director of the United States Patent and Trademark Office*